US011253260B2

(12) United States Patent
Kassab et al.

(10) Patent No.: US 11,253,260 B2
(45) Date of Patent: *Feb. 22, 2022

(54) METHODS FOR DIAGNOSING AND DELIVERING THERAPEUTIC INTERVENTIONS IN THE PERITONEAL CAVITY

(71) Applicant: CVDevices, LLC, San Diego, CA (US)

(72) Inventors: Ghassan S. Kassab, La Jolla, CA (US); Jose A. Navia, Sr., Buenos Aires (AR)

(73) Assignee: CVDevices, LLC, San Diego, CA (US)

( * ) Notice: Subject to any disclaimer, the term of this patent is extended or adjusted under 35 U.S.C. 154(b) by 328 days.

This patent is subject to a terminal disclaimer.

(21) Appl. No.: 16/365,357

(22) Filed: Mar. 26, 2019

(65) Prior Publication Data

US 2019/0216461 A1 Jul. 18, 2019

Related U.S. Application Data

(63) Continuation of application No. 14/617,066, filed on Feb. 9, 2015, now Pat. No. 10,238,392, which is a
(Continued)

(51) Int. Cl.
*A61B 17/11* (2006.01)
*A61B 17/12* (2006.01)
(Continued)

(52) U.S. Cl.
CPC .... *A61B 17/1114* (2013.01); *A61B 17/12031* (2013.01); *A61B 17/12099* (2013.01);
(Continued)

(58) Field of Classification Search
CPC ................. A61B 17/11; A61B 17/1114; A61B 17/12031; A61B 17/12099;
(Continued)

(56) References Cited

U.S. PATENT DOCUMENTS 6,248,117 B1 6/2001 Blatter
6,338,345 B1 1/2002 Johnson et al.
(Continued)

FOREIGN PATENT DOCUMENTS

WO   WO 01/89393 A1   11/2001
WO   WO 2006/108050 A3   10/2006
WO   WO 2007/005103 A2   1/2007

OTHER PUBLICATIONS

International Searching Authority, International Search Report, PCT/US2007/015207, dated Sep. 11, 2008.
(Continued)

*Primary Examiner* — Kathleen S Holwerda
(74) *Attorney, Agent, or Firm* — William F. Ward

(57) ABSTRACT

A device and system are described that are capable of isolating at least one targeted tissue and forming an anastomosis between two internal body structures though a completely endoscopic procedure. Further, the device and system described generally comprise two tubular members that are capable of moving in a telescopic fashion relative to one another. Additionally, a method is described for using the device and/or system to bypass the duodenum from digestion.

17 Claims, 23 Drawing Sheets

Related U.S. Application Data continuation of application No. 12/667,183, filed as application No. PCT/US2008/068852 on Jun. 30, 2008, now abandoned.

(60) Provisional application No. 60/974,387, filed on Sep. 21, 2007.

(51) Int. Cl.
*A61B 17/30* (2006.01)
*A61B 17/34* (2006.01)
*A61B 17/00* (2006.01)

(52) U.S. Cl.
CPC ........ *A61B 17/12172* (2013.01); *A61B 17/30* (2013.01); *A61B 17/3417* (2013.01); *A61B 17/3478* (2013.01); *A61B 2017/00278* (2013.01); *A61B 2017/1139* (2013.01); *A61B 2017/306* (2013.01); *A61B 2017/3488* (2013.01)

(58) Field of Classification Search
CPC .............. A61B 17/12172; A61B 17/30; A61B 17/3417; A61B 17/3478; A61B 2017/00278; A61B 2017/1139; A61B 2017/306; A61B 2017/3488; A61B 1/00; A61B 1/0087; A61B 1/00094; A61B 1/00135; A61B 1/005; A61B 1/012; A61B 1/018; A61B 1/273; A61B 1/2733; A61B 1/2736; A61B 1/31
See application file for complete search history.

(56) References Cited

U.S. PATENT DOCUMENTS

| | | |
|---|---|---|
| 6,517,477 B1 | 2/2003 | Wendlandt |
| 6,602,263 B1 | 8/2003 | Swanson et al. |
| 6,626,930 B1 | 9/2003 | Alien et al. |
| 6,702,828 B2 | 3/2004 | Whayne |
| 6,740,098 B2 | 5/2004 | Abrams et al. |
| 6,773,440 B2 | 8/2004 | Gannoe et al. |
| 6,866,674 B2 | 3/2005 | Galdonik et al. |
| 7,141,055 B2 | 11/2006 | Abrams et al. |
| 7,306,614 B2 | 12/2007 | Weller et al. |
| 10,238,392 B2 * | 3/2019 | Kassab ............... A61B 17/1114 |
| 2003/0187460 A1 * | 10/2003 | Chin ................ A61B 17/00008 606/129 |
| 2004/0116897 A1 * | 6/2004 | Aboul-Hosn ...... A61B 17/3421 604/508 |
| 2005/0043720 A1 * | 2/2005 | Ishikawa ............. A61B 17/1114 606/1 |
| 2005/0149073 A1 | 7/2005 | Arani et al. |
| 2006/0036267 A1 | 2/2006 | Saadat |
| 2006/0111733 A1 | 5/2006 | Shriver |
| 2006/0116749 A1 | 6/2006 | Willink et al. |
| 2006/0206123 A1 | 9/2006 | Brenneman |
| 2007/0135803 A1 * | 6/2007 | Belson ............... A61B 1/00128 606/1 |
| 2007/0198038 A1 | 8/2007 | Cohen et al. |
| 2007/0233162 A1 | 10/2007 | Gannoe et al. |
| 2007/0250083 A1 | 10/2007 | Deem et al. |
| 2007/0250113 A1 | 10/2007 | Hegeman et al. |
| 2007/0255273 A1 | 11/2007 | Fernandez et al. |
| 2008/0045859 A1 | 2/2008 | Fritsch et al. |
| 2008/0108871 A1 | 5/2008 | Mohr |
| 2008/0287907 A1 | 11/2008 | Gregory |

OTHER PUBLICATIONS

International Searching Authority, Written Opinion of the International Searching Authority, PCT/US2007/015207, dated Sep. 11, 2008.

Kantsevoy et al., "Endoscopic Gastrojejunostomy with Survival in a Porcine Model," Gastrointestinal Endoscopy, 2005, 62(2): 287-92; Am.Soc. for Gastrointestinl Endoscopy, Oak Brook, Illinois, USA.

Gauderer et al., "Gastrotomy Without Laparotomy: A Percutaneous Endoscopic Technique," J. Ped. Surgery, 1980, 15(6): 872-75, Grune & Stratton, Inc., New York, New York, USA.

Kalloo et al., "Flexible Transgastric Peritoneoscopy: A Novel Approach to Diagnostic and Therapeutic Interventions in the Peritoneal Cavity," Gastrointestinal Endoscopy, 2004, 60(1): 114-17, Am. Soc. for Gastrointestinal Endoscopy, Oak Brook, Illinois, USA.

Dray and Giday, "Notes: Where We Have Come From and Where We Are Going," Gastrointestinal Endoscopy, 2007, 66(5): 995-96, Am. Soc. for Gastrointestinal Endoscopy, Oak Brook, Illinois, USA.

Kalloo, A.N., "Editorial: Is STAT (Self-approximating Transluminal Access Technique) the First Step for Notes?," Gastrointestinal Endoscopy, 2007, 66(5): 979-80, Am. Soc. for Gastrointestinal Endoscopy, Oak Brook, Illinois, USA.

* cited by examiner

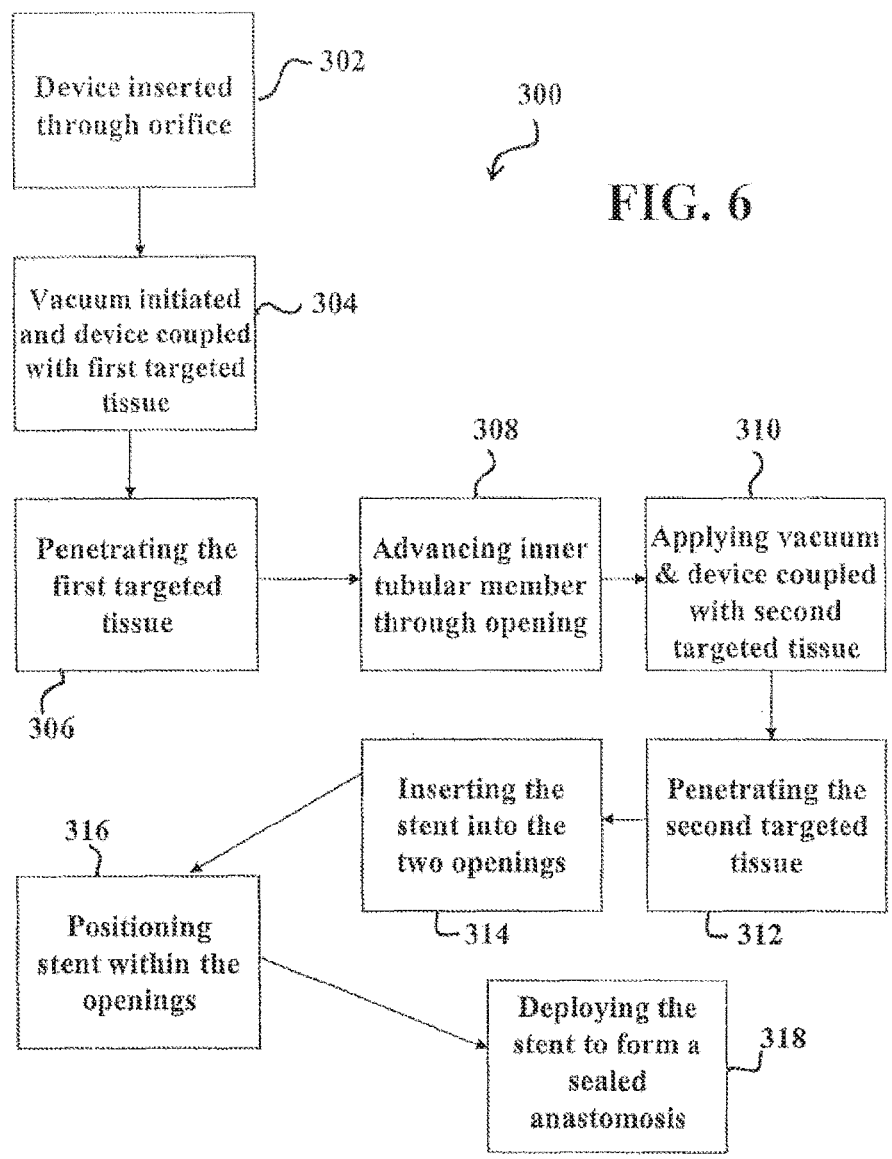

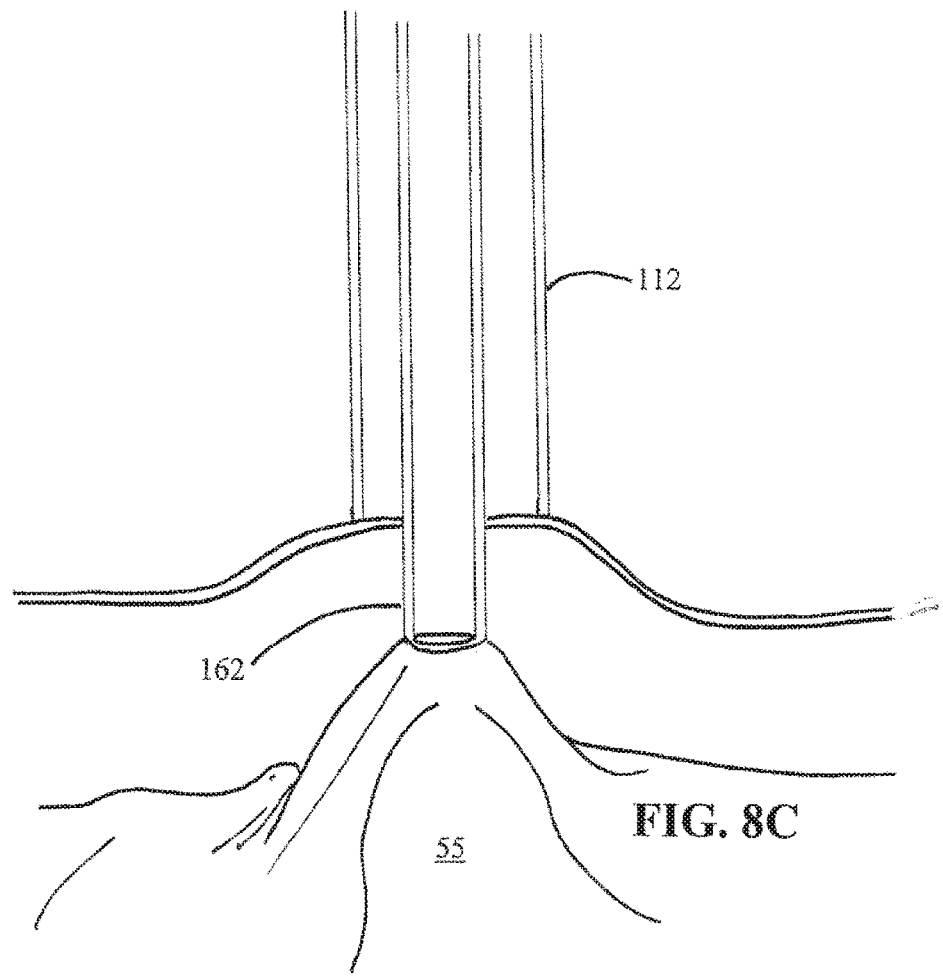

METHODS FOR DIAGNOSING AND DELIVERING THERAPEUTIC INTERVENTIONS IN THE PERITONEAL CAVITY

PRIORITY AND RELATED APPLICATIONS

The present application is related to, claims the priority benefit of, and is a U.S. continuation patent application of, U.S. patent application Ser. No. 14/617,066, filed Feb. 9, 2015 and issued as U.S. Pat. No. 10,238,392 on Mar. 26, 2019, which is related to, claims the priority benefit of, and is a U.S. continuation patent application of, U.S. patent application Ser. No. 12/667,183, filed Dec. 29, 2009, which is related to, and claims the priority benefit of, and is a U.S. § 371 application of, International Patent Application Serial No. PCT/US2008/068852, filed Jun. 30, 2008, which is related to, and claims the priority benefit of, a) U.S. Provisional Patent Application Ser. No. 60/974,387, filed Sep. 21, 2007, and b) International Patent Application Serial No. PCT/US2007/015207, filed Jun. 29, 2007, which is related to, and claims the priority benefit of, U.S. Provisional Patent Application Ser. No. 60/817,421, filed Jun. 30, 2006. Each of the aforementioned applications is incorporated herein by reference in their entirety.

BACKGROUND

Natural orifice transluminal endoscopic surgery ("NOTES") is a technique for diagnostic and therapeutic procedures whereby the peritoneal cavity, or the abdominal cavity, is penetrated through the gastrointestinal tract via a natural orifice. This differs from traditional open surgery, where a large incision is performed in the abdominal wall. NOTES also significantly differs from traditional laparoscopic surgery, which is a minimally invasive surgical technique that involves the introduction of a laparoscope into the body cavity through multiple small incisions in the abdominal wall. Laparoscopic access to the peritoneal cavity has, in many cases, proven superior to traditional open surgery as small incisions in the abdominal wall decrease postoperative pain and the risk of ventral herniation, diminish local and systemic complications, and provide an exceptional cosmetic result in comparison with open surgery. Patients also exhibit fewer postoperative ileus and recuperate rapidly after laparoscopic procedures.

NOTES represents a paradigm shift in minimally invasive surgeries and could potentially lead to a transformation in traditional endoscopy. (Giday et al. 2007). Generally, NOTES is a surgical technique whereby "scarless" abdominal operations can be performed using an endoscope that is passed through a natural orifice (e.g., mouth, urethra, anus, etc.) and advanced through an internal incision in the applicable organ or tissue (e.g., stomach, vagina, bladder or colon), thereby avoiding any external incisions or scarring. Accordingly, NOTES further decreases the invasiveness of abdominal surgeries by eliminating the need for abdominal incisions and further reducing the risk of post operative complications such as hernias and wound infections. (Kalloo 2007). In addition, NOTES has been associated with lower anesthesia requirements, faster recovery and shorter hospital stays, less immunosuppression and better postoperative pulmonary and diaphragmatic function. However, due to the nature of the procedure, it is of vital importance to have advanced flexible endoscopic tools and skills in order to accurately perform NOTES. (Giday et al. 2007).

The first transgastric endoscopic procedure was described in 1980, which reported the endoscopic insertion of a gastric feeding tube without the use of a laparotomy. (Gauderer et al. 1980; Giday et al. 2007). Successful acute studies have been performed in animal models, including transgastric liver biopsy, tubal ligation, gastrojejunostomy, cholecystectomy, splenectomy, partial hysterectomy and lymphadenectomy. There are also reports from India of transgastric appendectomy and tubal ligation in humans. (Giday et al. 2007). Further, a peroral endoscopic approach to the peritoneal cavity passing through an incision in the gastric wall has been successfully demonstrated in a porcine model. (Kalloo et al. 2004).

It is conventionally accepted that gastric remodeling can, in some cases, have a positive impact on patients who suffer from metabolic disorders and/or who are obese or morbidly obese. For example, evidence indicates that duodenal-jejunal exclusion exerts a direct impact on glucose tolerance in diabetic patients. Accordingly, and among other things, this implies that Type 2 diabetes mellitus may be rectified through surgical operations that bypass the proximal small bowel. The Roux-en-Y gastric bypass procedure ("RYGBP") is one such procedure that has been conventionally used for obese and morbidly obese patients in order to promote weight loss and to diminish the negative health effects commonly associated with obese and morbidly obese patients.

The use of NOTES to perform RYGBP or other related procedures may prove advantageous over conventional techniques known in the art. Particularly, there are some cases where transluminal access to the peritoneal cavity may be preferred over the transcutaneous route. For example, a transgastric approach may reduce the risk of postoperative wound complications in patients who are morbidly obese, as well as in patients who have anterior abdominal wall infection or severe scarring. (Giday et al. 2007).

At least one of the complications associated with a RYGBP is the development of an anastomotic stricture at the site of a gastrojejunostomy. Such strictures are related to substantial morbidity. While diverse techniques exist for creating the gastrojejunal anastomosis in an attempt to decrease complication rates (including hand-sewing or use of a circular or linear stapler), a thirty-one percent (31%) complication rate has been observed in patients following a RYGBP with the patients developing gastrojejunal anastomotic strictures. (Carrodeguas et al. 2006). Further, many of these strictures were observed in patients more than thirty (30) days after the procedure (7.3%). (Carrodeguas et al. 2006).

Various factors account for this high complication rate. Primarily, various unresectable primary (e.g., gastric, duodenal, pancreatic) or metastatic (e.g., colorectal or renal) malignancies can generate gastric outlet and duodenal obstruction. (Carrodeguas et al. 2006; Gauderer et al. 1980; Giday et al. 2007). Further, once such an obstruction occurs, open surgery for palliation of the obstruction is related to high morbidity and mortality. (Haugh et al. 2006; Kalloo 2007). Although the laparoscopic approach is less traumatic than open surgery, the laparoscopic creation of a gastrojejunostomy is technically difficult as it requires extensive surgical and laparoscopic skills. In addition, the use of a laparoscopic technique to perform such a procedure is related to numerous complications such as anastomotic stricture (3.1% to 8.8%) and leak (1.2% to 3.0%), (Kantsevoy et al. 2005).

BRIEF SUMMARY

Devices, systems and methods for performing a minimally invasive endoscopic surgery without the use of sutures or staples. Certain devices and systems comprise an endoscopic device for achieving an anastomosis without the use of sutures or staples, and that may be delivered through a natural orifice endoscopic surgical procedure. Further, devices are provided for isolating a tissue through an endoscopic procedure. Such devices as described herein comprise an outer tubular member configured to be placed within a lumen and advanced endoscopically therethrough. The outer tubular member comprises a first vacuum channel, a first compartment, a first end and a second end, with the first vacuum channel and the first compartment extending to the second end of the outer tubular member. A first vacuum port that is capable of being operatively connected to a vacuum source may further be coupled with the outer tubular member in such a manner that the first vacuum port is in communication with the interior of the first vacuum channel. In addition, the first vacuum channel may comprise a first suction port disposed at or near the second end of the outer tubular member. The first suction port is configured to removably couple with a targeted tissue such that the first suction port can form a reversible seal therewith when suction is applied through the first vacuum channel (through operation of the vacuum source or otherwise).

The endoscopic device may also comprise an inner tubular member that is slidably disposed within the interior of the first compartment of the outer tubular member. The inner tubular member comprises a second vacuum channel, a second compartment, a first end and a second end, wherein the second vacuum channel and the second compartment extend to the second end of the inner tubular member. As previously noted, the inner tubular member is slidably disposed within the interior of the first compartment of the outer tubular member. When a user operates the device, the second end of the inner tubular member is capable of being advanced through the second end of the outer tubular member, such that the inner tubular member extends in a telescopic fashion distally of the second end of the outer tubular member.

The devices and systems may further include at least one instrument slidably disposed within the inner tubular member of the endoscopic device. In one example, at least one of the at least one instruments comprises a catheter having a first end and a second end. In this example, the second end of the catheter may comprise a means for penetrating tissue, such as a needle. Further, the catheter may also comprise a means for dilation, such as an inflatable balloon or other device. In this example, the balloon is coupled with the second end of the catheter (proximal to the means for penetration), and the balloon is capable of moving between a deflated position and an inflated position. Accordingly, when the catheter is slidably moved within the second compartment of the inner tubular member, the second end of the catheter comprising the means for penetration and the means for dilation can be advanced through the second ends of both the inner and outer tubular members.

At least one of the at least one instruments of the endoscopic devices and systems described herein may comprise an optic system instrument. The optic system instrument may comprise any optic system known in the art that is capable of endoscopic insertion into a body. For example, and without limitation, the optic system instrument may comprise a fibroscope. When slidably disposed within the interior of the inner tubular member, the optic system instrument can be used to facilitate the navigation of the second end of the outer tubular member through the body, localize the targeted tissue, facilitate the navigation and use of the at least one instruments disposed within the second compartment of the inner tubular member, and/or facilitate the navigation of the second end of the inner tubular member.

Additionally, at least one of the at least one instruments of the endoscopic devices and systems described herein may comprise a stent delivery device. The stent delivery device may comprise a first end and a second end, wherein the second end of the stent delivery device is configured to removably couple with a stem for forming an anastomosis. The stent may comprise a ring configuration and be capable of moving between a first compressed position and a second extended position. Further, the stent is capable of deploying between at least two openings in tissues and to form a sealed anastomosis therebetween. The stent may be an auto expandable cover stent such that when the stent is released from the stem delivery device, the stent will automatically deploy and thereby securely couple with the surrounding tissues. Further, the stent may be comprised of polyurethane, polytetrafluoroethylene, or any other suitable material in the medical arts.

Systems are also provided for forming an anastomosis between two tissues and/or organs through a completely endoscopic procedure. Such systems comprise the various components discussed above, including the stem for placement between a first opening in a first tissue and a second opening in a second tissue. Further, systems are provided for bypassing the duodenum from digestion.

Methods are also provided for forming an anastomosis between two tissues and/or organs and/or bypassing the duodenum from digestion. The method may comprise the steps of providing the above described devices and systems; inserting the endoscopic device through an aperture in the body of a patient; supplying suction through the first vacuum port such that the first suction port of the outer tubular member forms a reversible seal with the first targeted tissue; penetrating the first targeted tissue with the means for penetrating of the catheter such that the first opening is formed in the first targeted tissue; advancing the inner tubular member through the second end of the outer tubular member and through the first opening in the first targeted tissue; supplying suction through the second vacuum port such that the second suction port of the inner tubular member forms a reversible seal with the second targeted tissue; penetrating the second targeted tissue with the means for penetrating of the catheter such that a second opening is formed in the second targeted tissue; slidably inserting the stent delivery device and the stent into the interior of the inner tubular member; positioning the stent partially within the first and second openings; and deploying the stent to form a sealed anastomosis between the first and second openings. In at least one embodiment of the method, the first targeted tissue comprises an interior wall of a stomach and the second targeted tissue comprises an exterior wall of a proximal jejunum. In this manner, an anastomosis is formed between the stomach and proximal jejunum such that the interiors of both organs are in communication with each other.

In addition to the above-listed steps, the method may further comprise the step of manipulating the inner and outer tubular members such that the first and second openings are positioned in close proximity and in substantially concentric alignment with one another. In this manner, the endoscopic device and/or system can be used to displace a portion of the jejunum from its anatomical position such that the second opening therein can communicate with the stomach. Additionally, the method may further comprise the step of inserting a stem into a pylorus of the stomach such that the pyloric portion is occluded and digested matter is substantially prevented from flowing therethrough. In this manner, the digested matter in the stomach may flow directly into the proximal jejunum by way of the anastomosis.

The method may further comprise the steps of advancing a balloon configured in a first deflated position through the second ends of the inner and outer tubular members and into the first opening of the first targeted tissue; dilating the balloon into the second inflated position such that the first opening increases in diameter; deflating and advancing the balloon through the second end of the inner tubular member and into the second opening of the second targeted tissue; and, dilating the balloon into the second inflated position such that the second opening increases in diameter.

Methods for isolating tissue are also described, with certain embodiments comprising the steps of providing the device described above; inserting the device into an orifice of a patient; attaching the first suction port on or near a targeted tissue; operatively connecting a vacuum source to the vacuum port such that the suction port removably attaches to the targeted tissue; and manipulating the position of the targeted tissue.

BRIEF DESCRIPTION OF THE DRAWINGS

FIG. 6 shows a flow chart of a method for using the endoscopic device of FIGS. 2A-5A;

FIGS. 8A to 8C show the formation of an opening in a targeted tissue and the localization of the second targeted tissue using the endoscopic device disclosed herein;

DETAILED DESCRIPTION

It will be appreciated by those of skill in the art that the following detailed description of the disclosed embodiments is merely exemplary in nature and not intended to limit the scope of the appended claims.

The disclosed embodiments include devices, systems, and methods useful for accessing various tissues endoscopically. For ease of description, the embodiments of the endoscopic device described herein may be described with the term "distal" as referring toward the end which is inserted in the patient and the term "proximal" as referring to the end which remains outside of the patient.

Figure 1A:
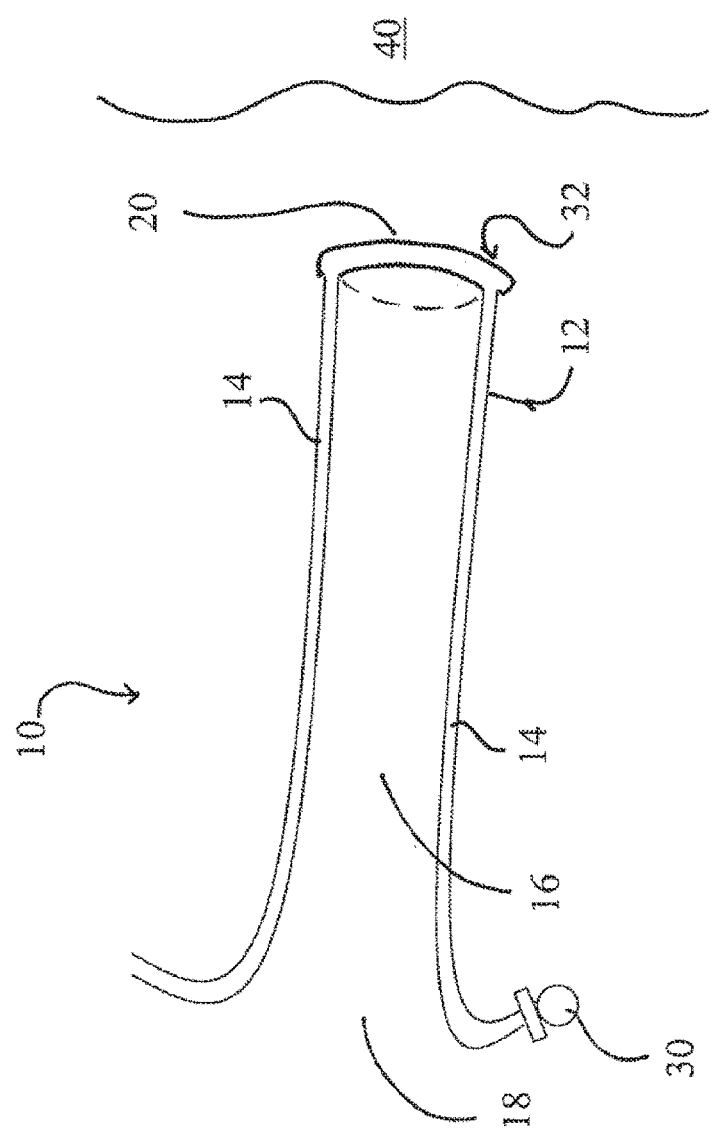
FIG. 1A shows a cross-sectional view of an embodiment of an endoscopic device as disclosed herein.
Figure 1B:
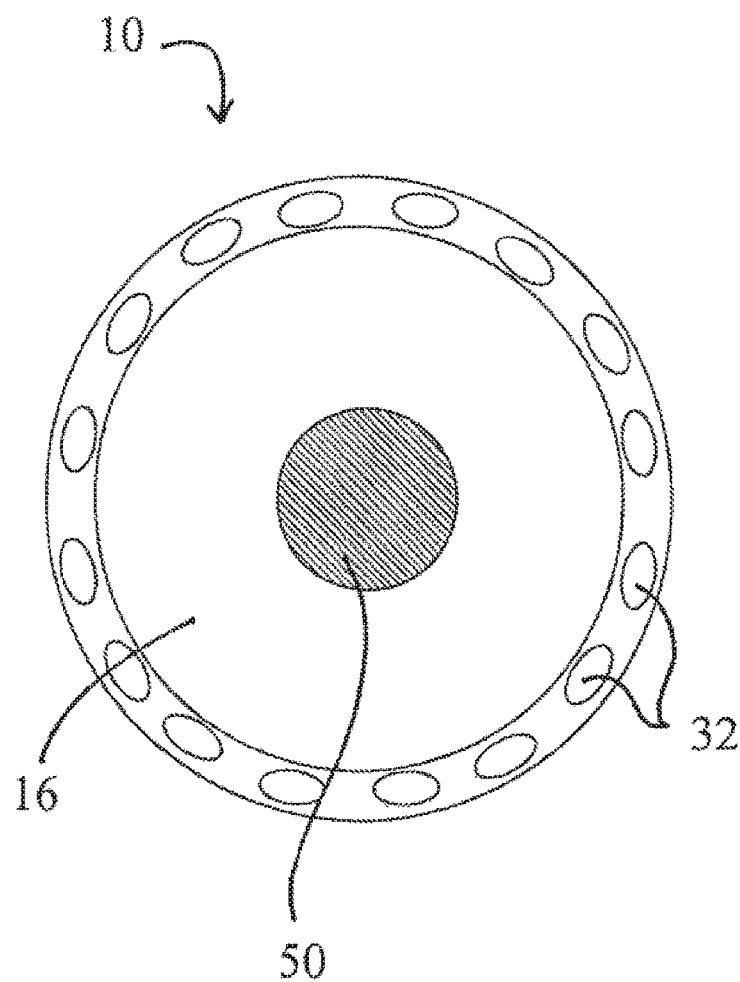
FIG. 1B shows a bottom view of the second end of the endoscopic device of FIG. 1A, further comprising an instrument disposed therein.

One embodiment of an endoscopic device 10 is shown in FIGS. 1A and 1B. The endoscopic device 10 comprises a tubular member 12 configured as an elongated tube having an interior, a first end 18 and a second open end 20. The tubular member 12 may be flexible such that the tubular member 12 can be manipulated through various body spaces such as lumens and cavities.

The interior of the tubular member 12 comprises a vacuum channel 14 and a compartment 16, both the vacuum channel 14 and the compartment 16 each defining an interior space. In the embodiment shown in FIGS. 1A and 1B, the vacuum channel 14 is disposed around the circumference of the tubular member 12 and the compartment 16 is disposed within the interior of the tubular member 12 such that the compartment 16 is wholly surrounded by the vacuum channel 14. It will be appreciated that the vacuum channel 14 and the compartment 16 may be disposed in any fashion within the interior of the tubular member 12 so long as the vacuum channel 14 extends to the second open end 20 of the tubular member 12. For example, although the first vacuum channel 14 and the first compartment 16 are shown in FIG. 1A as extending from the first end 18 of the tubular member 12 along a substantial portion of the length of the tubular member 12, the vacuum channel 14 and the compartment 16 may or may not span the entire length of the tubular member 12. Particularly, the vacuum channel 14 and the compartment 16 do not necessarily extend to the first end 18 in order to ensure that suction may be distributed relatively evenly around the circumference of the tubular member 12 through a suction port 32.

The tubular member may further comprise a vacuum port 30 coupled with the vacuum channel 14 capable of operative connection with a vacuum source. The vacuum channel 14 is disposed in a location proximate to the first end 18 of the tubular member 12. A syringe or other vacuum source (not shown) may be coupled to the vacuum channel 14 through the vacuum port 30 in order to provide appropriate suction through the vacuum channel 14. It will be understood that any type of vacuum source may be used to supply suction through the vacuum channel 14, such as a controlled vacuum system providing specific suction pressures. At the second end 20 of the tubular member 12, a suction port 32 is attached to the vacuum channel 14 for contacting a targeted tissue 40. The suction port 32 may comprise any configuration that is capable of removably attaching to the targeted tissue 40 such that a reversible seal between the second end 20 of the tubular member 12 and the targeted tissue 40 is formed when the vacuum source is activated and coupled with the vacuum port 30. In one embodiment, the targeted tissue 40 comprises an organ or tissue generally, however, in an alternative embodiment the targeted tissue 40 may comprise a location so specific that when suction port 32 is applied to the targeted tissue 40, the targeted tissue 40 is thereby encompassed within the circumference of the suction port 32.

Now referring to FIG. 1B, an additional embodiment of the endoscopic device 10 is shown. The endoscopic device 10 may further comprise a optic system instrument 50 slidably disposed within the interior of compartment 16 and terminating adjacent to the second end 20 of the tubular member 12. The optic system instrument 50 may be any fluoroscope, fibroscope, endoscopic transilluminator, or other device so long as the instrument is capable of being slidably received through the compartment 16 of the tubular member 12 and functions to facilitate the navigation of the endoscopic device 10 with respect to the targeted tissue 40.

Figure 1C:
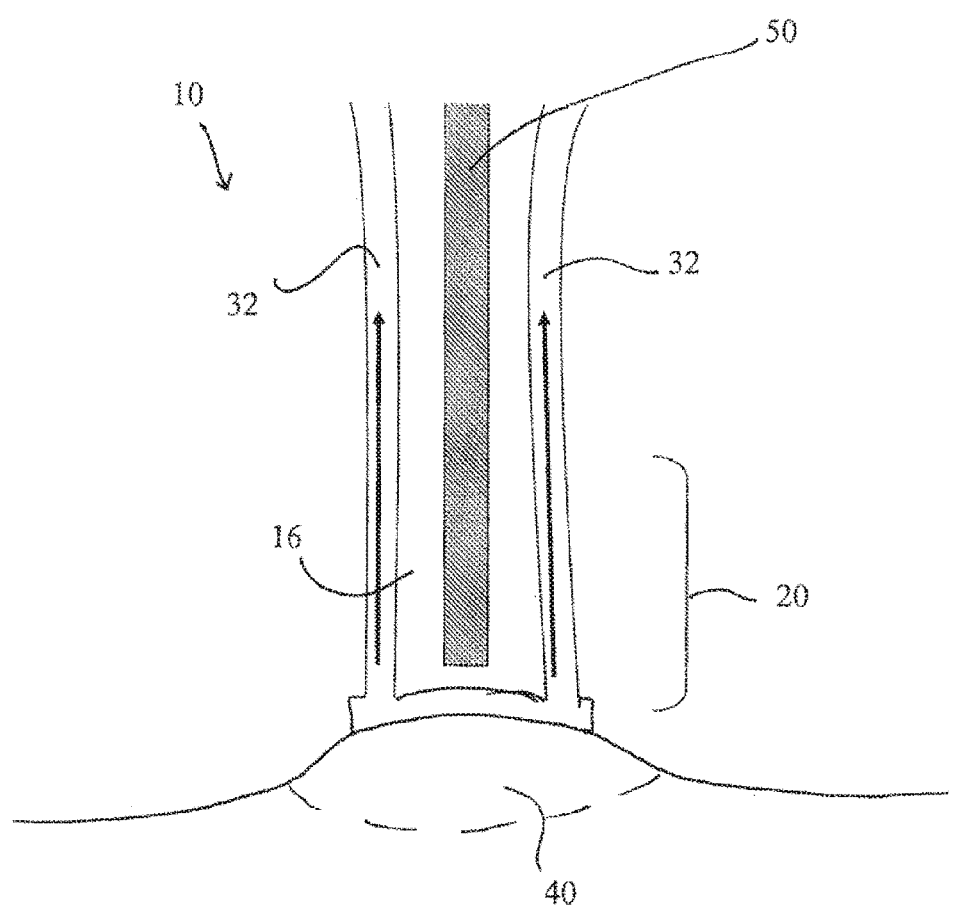
FIG. 1C shows a cross-sectional view of an additional embodiment of the endoscopic device of FIG. 1B.

Referring now to FIG. 1C, the endoscopic device 10 is placed via standard approach into the appropriate orifice (the particular orifice depending upon the location of the targeted tissue 40). As previously noted, the endoscopic device 10 may be positioned under fluoroscopic or fibroscopic guidance to achieve a desired position (i.e. adhere to a specific targeted area). The endoscopic device 10 is advanced through the lumen or cavity of the patient until the second open end 20 is positioned adjacent to or in contact with the targeted tissue 40. Upon positioning the second open end 20 of the tubular member 12 in the desired location, the vacuum source (not shown is operatively connected to the vacuum port 30 (see FIG. 1A) such that suction is initiated through the vacuum channel 14. The force of the suction is represented in FIG. 1C as upward arrows within the vacuum channel 14, and is of sufficient amplitude to attach the targeted tissue 40 to the second open end 20 of the tubular member 12 such that a reversible seal is formed therebetween.

In one application, the endoscopic device 10 may be used to manipulate the position of the targeted tissue 40. For example, it is often necessary to perform a surgical procedure on a targeted organ or tissue that is positioned adjacent to an organ or tissue that is not to be surgically treated. Accordingly, the endoscopic device 10 may be employed to temporarily move the targeted tissue or organ away from the other organ/tissue such that the desired procedure can be performed, while minimizing the affect to the untargeted organ or tissue. It will be recognized that this procedure may be used with any organ and/or tissue in the body and is especially useful if a surgeon is required to perform highly accurate incisions on an area closely surrounded by other tissue and/or organs.

In this embodiment, the endoscopic device 10 is attached to the first targeted organ or tissue as previously described. Thereafter, pressure is applied to the first end 18 of the endoscopic device 10 to manipulate the first targeted organ or tissue such that space is created or enlarged between the first targeted tissue and the untargeted organ or tissue. For example, if an incision is desired to be made in the gastric wall, but it is preferred not to cause trauma to the small intestine disposed proximally thereto, the endoscopic device 10 may be attached to the interior gastric wall through the application of suction through the suction port 32, and the endoscopic device 10 may then be slightly retracted to pull the gastric wall away from the small intestine. In this manner, space is created between the surrounding organs and tissues, and incisions and/or surgical repair can be effectuated to the gastric wall without risking trauma to the underlying small intestine. Accordingly, the use of endoscopic device 10 to manipulate the position of organs and/or tissue within the body can decrease the risk of trauma to organs and/or tissue that are in the general vicinity of the targeted tissue. It will be recognized that the endoscopic device 10 may be used with any organs and/or tissue within the body and the examples contained herein are solely for explanatory purposes and not intended to be limiting.

Figure 2A:
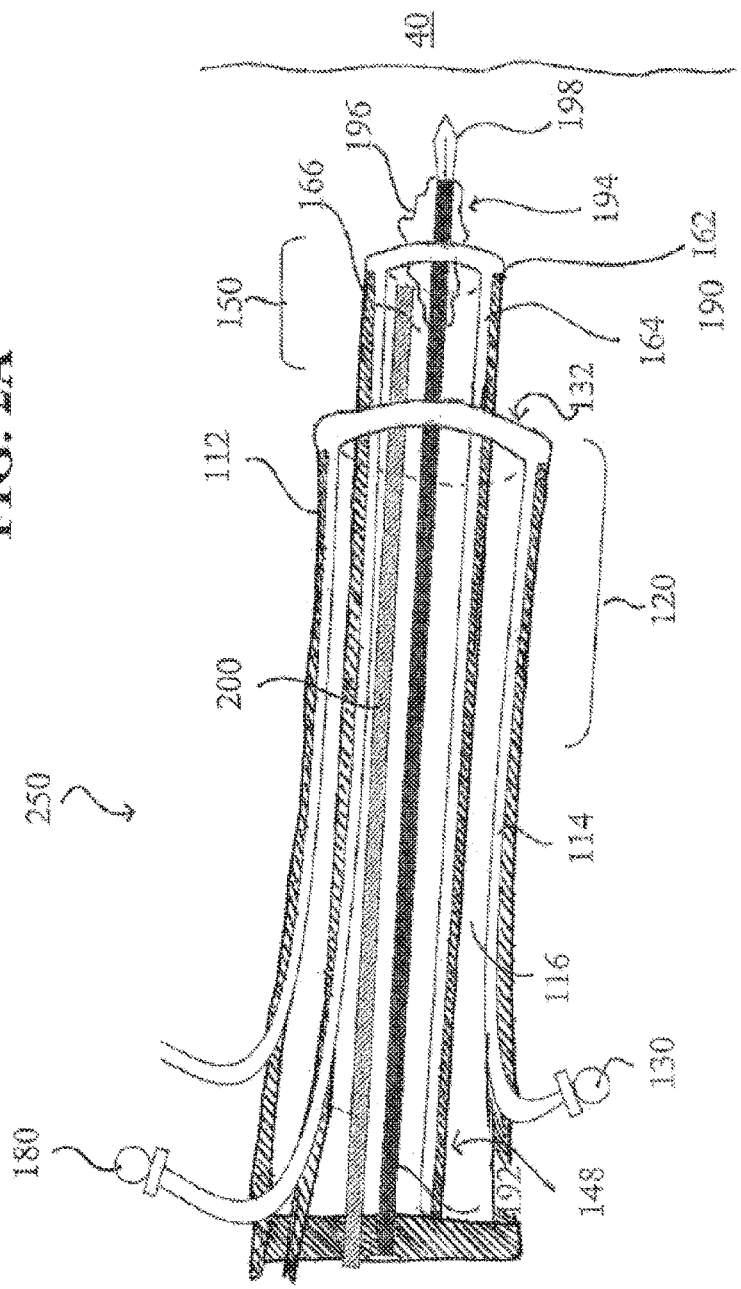
FIG. 2A shows a cross-sectional view of another embodiment of the endoscopic device disclosed herein.
Figure 2B:
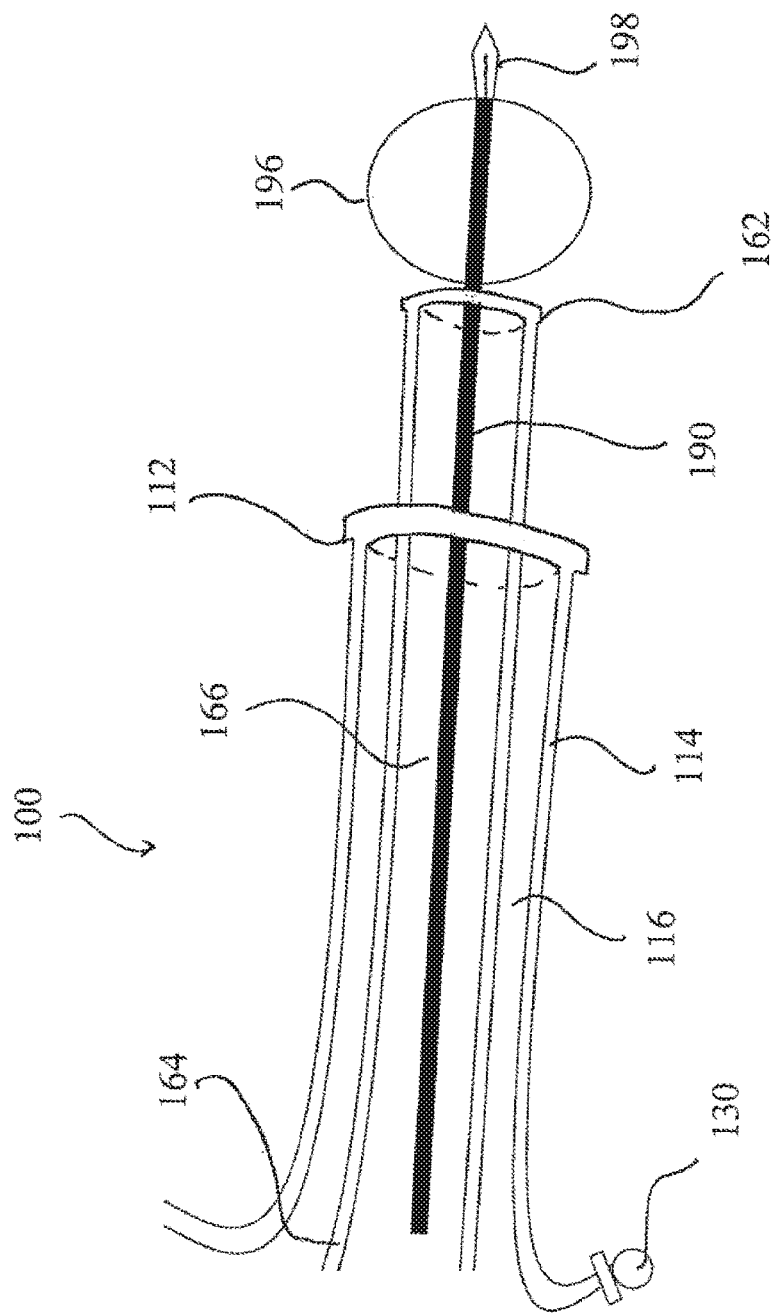
FIG. 2B shows a cross-sectional view of the endoscopic device of FIG. 2A in a different position.

Now referring to FIGS. 2A and 2B, an alternative embodiment of an endoscopic device 100 is shown. The endoscopic device 100 comprises two coaxial tubes mounted for relative telescoping motion and, in part, utilizes vacuum pressure to attach to internal tissue. Specifically, the endoscopic device 100 comprises an outer tubular member 112, an inner tubular member 162, a first vacuum port 130, and a second vacuum port 180. The outer tubular member 112 is configured identically to the tubular member 12 of endoscopic device 10 such that the outer tubular member 112 comprises an elongated tube having an interior, a first end 118 and a second open end 120. The outer tubular member 112 may also be flexible such that the outer tubular member 112 can be manipulated through various body spaces such as lumens and cavities.

The interior of the outer tubular member 112 comprises a first vacuum channel 114 and a first compartment 116, both the first vacuum channel 114 and the first compartment 116 each defining an interior space. In the embodiment shown in FIGS. 2A and 2B, the first vacuum channel 114 is disposed around the circumference of the outer tubular member 112 and the first compartment 116 is disposed within the interior of the outer tubular member 112 such that the first compartment 116 is wholly surrounded by the first vacuum channel 114. It will be appreciated that the first vacuum channel 114 and the first compartment 116 may be disposed in any fashion within the interior of the outer tubular member 112 so long as the first vacuum channel 114 extends to the second open end 120 of the outer tubular member 112. Although the first vacuum channel 114 and the first compartment 116 extend from the first end 118 of the outer tubular member 112 along a substantial portion of the length of the outer tubular member 112, the first vacuum channel 114 and the first compartment 116 may or may not span the entire length of the outer tubular member 112. Particularly, the first vacuum channel 114 and the first compartment 116 do not necessarily extend to the first end 118 in order to ensure that suction may be distributed relatively evenly around the circumference of the outer tubular member 112 through a suction port 132.

The outer tubular member 112 may further comprise a first vacuum port 130 coupled with the first vacuum channel 114 in a location adjacent to the first end 118 of the outer tubular member 112. The first vacuum port 130 is capable of operative connection with an external vacuum source. A syringe or other vacuum source (not shown) may be coupled to the first vacuum channel 114 through the first vacuum port 130 to provide the appropriate suction through the first vacuum channel 114. It will be understood that any type of vacuum source may be used to supply suction through the first vacuum channel 114, such as a controlled vacuum system providing specific suction pressures. At the second end 120 of the outer tubular member 112, a first suction port 132 is attached to the first vacuum channel 114 for contacting a targeted tissue 40 (see FIG. 2C). The first suction port 132 may comprise any configuration that is capable of removably attaching to the targeted tissue 40 such that a reversible seal is formed between the targeted tissue 40 and the second end 120 when the vacuum source is activated and coupled with the first vacuum port 130.

The inner tubular member 162 is slidably disposed within the interior of the first compartment 116 and comprises an elongated tube having an interior, a first end 148, and a second open end 150. Similar to the outer tubular member 112, the inner tubular member 162 may be flexible such that the outer tubular member 112 can be manipulated through various body spaces such as lumens and cavities. Furthermore, the second open end 150 of the inner tubular member 162 is capable of slidably extending distally of the second open end 120 of the outer tubular member 112 in a telescoping fashion.

The interior of the inner tubular member 162 comprises a second vacuum channel 164 and a second compartment 166, both the second vacuum channel 164 and the second compartment 166 each defining an interior space. The interior space of the second compartment 166 may be further configured to slidably receive at least one instrument therein.

Figure 2C:
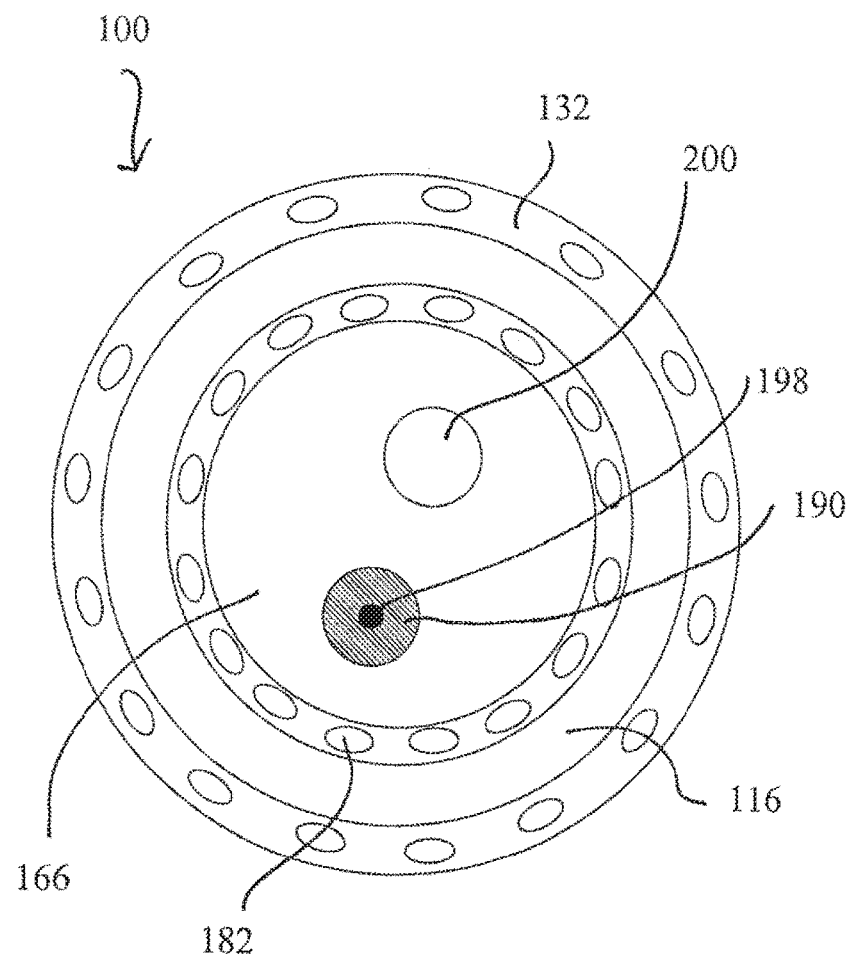
FIG. 2C shows a bottom view of the second end of the endoscopic device shown in FIGS. 2A and 2B.

In the embodiments shown in FIGS. 2A, 2B, and 2C, the second vacuum channel 164 is disposed around the circumference of the inner tubular member 162 and the second compartment 166 is disposed within the interior of the inner tubular member 162 such that the second compartment 166 is wholly surrounded by the second vacuum channel 164. Further, the inner tubular member 162 and the second compartment 166 share a concentric linear axis. It will be appreciated that the second vacuum channel 164 and the second compartment 166 may be disposed in any fashion within the interior of the inner tubular member 162 so long as the second vacuum channel 164 extends to the second open end 150 of the inner tubular member 162. Although the second vacuum channel 164 and the second compartment 166 are shown in FIG. 2A as extending from the first end 148 of the inner tubular member 162 along a substantial portion of the length of the inner tubular member 162, the second vacuum channel 164 and the second compartment 166 may or may not span the entire length of the inner tubular member 162. Particularly, the second vacuum channel 164 and the second compartment 166 do not necessarily extend to the first end 148 in order to ensure that the suction from the external vacuum source is distributed relatively evenly around the circumference of the outer tubular member 162 through a suction port 182 (discussed below).

The inner tubular member 162 may further comprise a second vacuum port 180 coupled with the second vacuum channel 164 in a location adjacent to the first end 148 of the inner tubular member 162. Similar to the first vacuum port 130, the second vacuum port 180 is capable of operative connection with an external vacuum source (not shown). The second vacuum port 180 may share the vacuum source with the first vacuum port 130, or the second vacuum port 180 may be coupled with an independent vacuum source. It will be understood that any vacuum source may be used so long as the vacuum source is capable of producing sufficient suction within the second vacuum channel 164.

At the second end 150 of the inner tubular member 162, a second suction port 182 is attached to the second vacuum channel 164 and configured to engage a targeted tissue 40. The second suction port 182 may comprise any configuration that is capable of removably attaching to the targeted tissue 40 such that a reversible seal is formed therebetween when the vacuum source is activated and coupled with the second vacuum port 180.

A variety of instruments may be used in conjunction with the endoscopic device 100 to form system 250. Such instruments may include, without limitation, an optic system instrument, a catheter, a balloon catheter, and/or a stent delivery device. For example, FIG. 2A illustrates the endoscopic device 100 employed in conjunction with a catheter 190. The catheter 190 is an elongated tube having a first end 192 and a second end 194. The diameter of the catheter 190 is less than the diameter of the second compartment 166 such that the catheter 190 can be inserted therein and easily moved through the interior of the second compartment 166. Further, the catheter 190 is disposed within the second compartment 166 such that the second end 194 of the catheter 190 is capable of being advanced and retracted through the second open end 150 of the inner tubular member 162.

As shown in FIGS. 2A and 2B, the catheter 190 may further include a means for dilating an opening and a means for penetrating the targeted tissue 40. The means for dilating an opening may comprise an expandable stent a clip, a balloon, or any other means known in the art. In one embodiment, the means for dilating an opening comprises a balloon 196. The balloon 196 is mounted about the periphery of the catheter 190 in a position adjacent to the second end 150; however, it is understood that the balloon 196 may be any balloon used in conjunction with a balloon catheter that is known in the art.

The balloon 196 may comprise a stiffening balloon that comprises a predetermined diameter and does not expand, or an inflating balloon. In the event an inflating balloon is used with the endoscopic device 100 disclosed herein, the balloon 196 may be employed within an aspiration tube in order to impose an upward limit on the balloon's inflated diameter.

When the balloon 196 comprises an expandable balloon, the balloon 196 is capable of moving between a first deflated position and a second inflated position. In this example the balloon 196 may further comprise a fluid passageway (not shown) that is in fluid communication with the balloon 196 such that the fluid passageway can be used to expand the diameter of the balloon 196. The fluid passageway may comprise a separate tubule carried by the catheter 190 or an independent tube disposed within the interior of the second compartment 166 of the inner tubular member 162.

The means for penetrating the targeted tissue 40 may comprise any means that is capable of cutting or piercing the targeted tissue. In one embodiment, the means for penetrating the targeted tissue comprises a needle 198. The needle 198 is attached to the second end 194 of the catheter 190, and located distally of the balloon 196. The needle 198 is disposed in a straightened configuration such that the needle 198 extends distally from the catheter 190. In an alternative embodiment, the catheter 190 further comprises a lumen (not shown) extending the length of the catheter 190, and the needle 198 is a hollow needle, the interior of which is in communication with the lumen of the catheter 190. In this manner, fluids (including, without limitation, gases) may be provided through the lumen of the catheter 190 and into the hollow needle 198 for delivery to the targeted tissue 40. The needle 196 may also be removable from the second end 194 of the catheter 190 and therefore may be easily replaced.

FIG. 2C shows a direct view of the distal end of the endoscopic device 100 wherein the endoscopic device 100 is employed with the catheter 190 and an optic system instrument 200. The optic system instrument 200 is configured identically to the optic system instrument 50 described with respect to FIGS. 1B and 1C, and such optic system instrument 200 may be used in conjunction with the catheter 190 to facilitate navigation of the endoscopic device 100 and/or the catheter 190, the second end 194 of the catheter 190, the balloon 196, and/or the needle 198. As shown in FIG. 2B, both the catheter 190 and the optic system instrument 200 are slidably disposed within the interior of the second compartment 166 of the inner tubular member 162.

Figure 3:
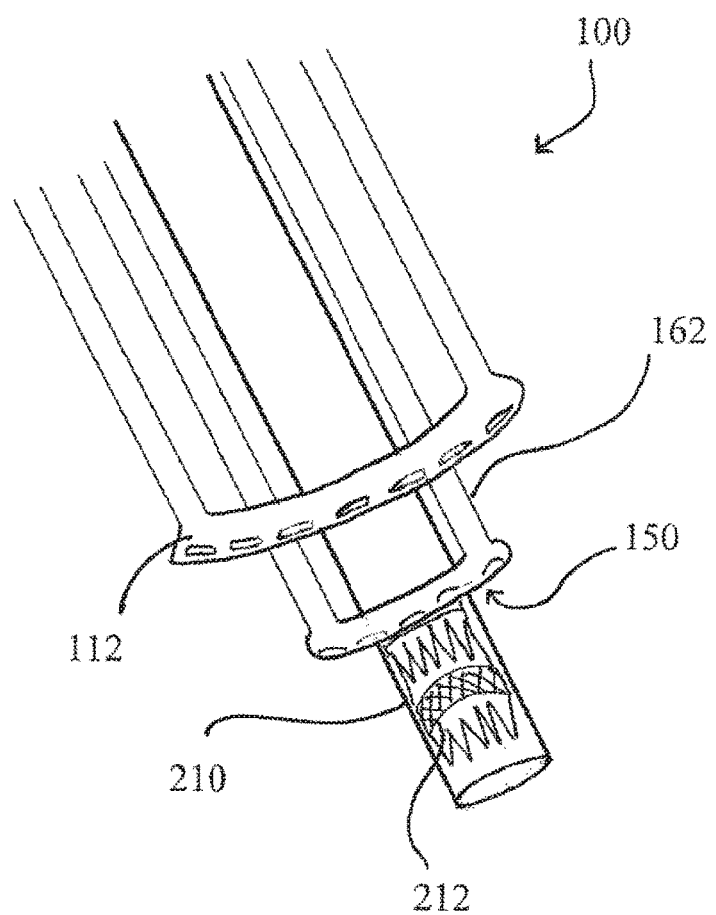
FIG. 3 shows a side view of an embodiment of the endoscopic device disclosed herein.

The endoscopic device 100 may further be used in conjunction with a stent delivery device 210, as shown in FIG. 3. The stent delivery device 210 comprises a tube having a proximal end and a distal end, wherein the distal end is configured to receive a stent 212. When employed within the second compartment 166 of the inner tubular member 162, the second end of the stent delivery device 210 is capable of being advanced and retracted through the second end 150 of the inner tubular member 162, such that the stein delivery device 210 and attached stent 212 extend distally from the endoscopic device 100. Similar to the other instruments disclosed herein, the diameter of the stent delivery device 210 is less than the diameter of the interior of the second compartment 166 such that the stent delivery device 210 can be slidably moved therethrough.

The stent 212 may be any stent known in the art, and in one embodiment, the stent 212 comprises an expandable metallic balloon stent. In an alternative embodiment, the stent 212 is either circular or elliptical in shape and comprises nickel-titanium alloy available under the trademark "NITINOL", stainless steel, ferromagnets, magnets, or bioabsorbable materials. The stent 212 may further be covered with polyurethane or polytetrafluoroethylene and, in one embodiment, is capable of grabbing tissue from both sides when the stent is deployed.

Figure 4A:
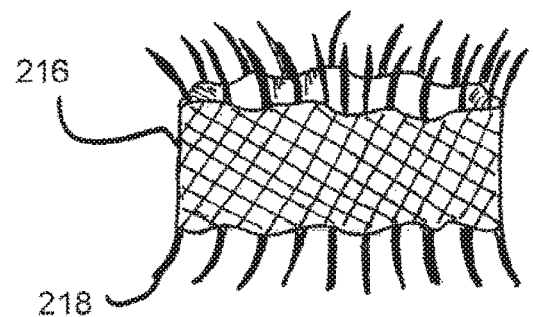
FIG. 4A to 4C show one embodiment of a stent used in conjunction with the endoscopic device disclosed herein.
Figure 4B:
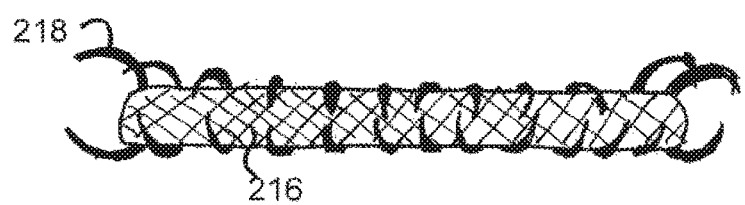

FIGS. 4A, 4B, and 5 illustrate various embodiments of the stent 212. As shown in FIG. 4, the stern 212 comprises a ring 216 and a plurality of hooks 218 extending from both ends of the ring 216. The diameter of the ring 216 expands when the stein 212 is deployed (as described below), and may be specifically selected based on the characteristics of the patient and the desired application.

Figure 4C:
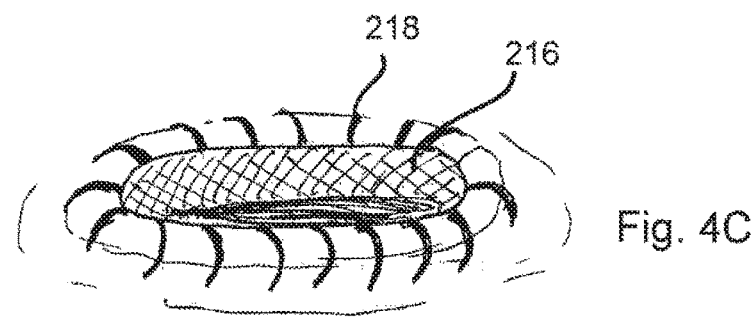

The stent 212 is movable between a first position and a second position. As shown in FIG. 4A, when the stent 212 is disposed in the first position, the plurality of hooks 218 extend in a direction substantially parallel to the axis of the ring 216 such that the stent 212 is elongated and comprises a narrower diameter. In the second position, as shown in FIG. 4B, the plurality of hooks 218 fold back on themselves and extend in a direction substantially perpendicular to the axis of the ring 216, and the ring 216 of the stent 212 expands radially, thereby increasing its diameter. When the stem 212 is in the second position, it is commonly referred to as being "deployed". Accordingly, when the stent 212 is in the second "deployed" position, the plurality of hooks 218 extend radially from both sides of the ring 216, thus effectively compressing whatever tissue is disposed therebetween, and the ring itself expands radially to firmly adhere within the edges of any opening into which it is inserted. For example, as shown in FIG. 4C, when the stent 212 is deployed within a tissue opening, the plurality of hooks 218 compress the tissue from above and below the tissue opening and thereby support the position of the stent therein.

Figure 5A:
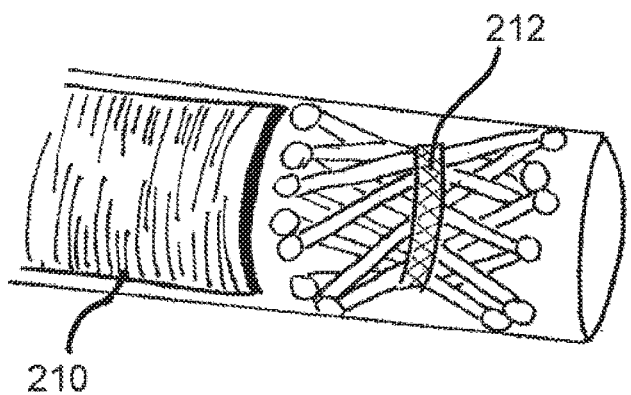
FIG. 5A shows an embodiment of a stent delivery device as disclosed herein.
Figure 5B:
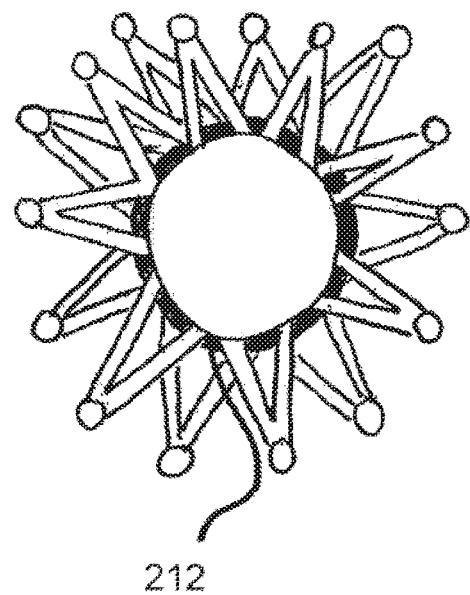
FIG. 5B shows a bottom view of the distal end of one embodiment of a stent forming an anastomosis.

Referring now to FIGS. 5A and 5B, an additional embodiment of the stent 212 is shown. In FIG. 5A, the stent 212 is coupled with the distal end of the stent delivery device 210. Here, the stein 212 is a pliable, spring-triggered stent and may comprise a nickel-titanium alloy, stainless steel, or other similar material. Due to the configuration of the stent 212 shown in FIGS. 5A and 5B, when the stent 212 is positioned in the first position (as shown in FIG. 5A), the stent 212 is spring compressed and, as such, storing mechanical energy. When disposed in this first position, the stent 212 comprises a narrower configuration that enables the stent 212 to be loaded into the end of the stent delivery device 210 and thus maneuvered through the body by way of the stent delivery device 210 and the endoscopic device 100. Upon release from the stent delivery device 210 (i.e. when the stent 212 is moved through the open distal end of the stent delivery device 210), the mechanical energy is released from the stent 212 and the plurality of hooks 218 extend outwardly from both sides of the ring 216 such that the stent 212 moves into the second position.

In another embodiment, the stent 212 comprises a nickel-titanium alloy which is affected by temperature. In this embodiment, the stent 212 is delivered in the first position and subsequently moves into the second position (as shown in FIG. 5B) when the stent 212 is subjected to body temperature. In yet another embodiment, the stent 212 may comprise at least two magnets. In this embodiment, the stent 212 is deployed by placing the magnets on opposite sides of an opening such that the magnets magnetically engage through the tissue, thereby compressing any tissue therebetween. Furthermore, it will be understood that the stent 212 may comprise any stent known in the art and is not limited to those embodiments described herein.

Each of the instruments disposed within the second compartment 166 may be independently inserted and/or withdrawn from the endoscopic device 100. For example, and without limitation, once the optic system instrument 200 has been used to position the endoscopic device 100 within a body cavity, the optic system instrument 200 may be withdrawn from the second compartment 166 and the catheter 190 may be placed therein. Alternatively, both the optic system instrument 200 and the catheter 190 may be initially disposed within the second compartment 166 and, after the optic system instrument 200 is used to position the endoscopic device 100, the optic system instrument 200 may be withdrawn from the second compartment 166 while the catheter 190 remains therein. It will be understood that any combination of instruments may be inserted and/or withdrawn into the second compartment 166 of the inner tubular member 162, independently or concurrently, so long as the inserted instruments can be slidably retracted and advanced through the interior of the second compartment 166.

In operation, the endoscopic device 100 may be used to perform surgical procedures completely endoscopically, even when the procedures involve more than one organ. For example, in at least one application, the endoscopic device 100 can be used for natural orifice transluminal endoscopic surgical procedures. While the endoscopic device 100 is described herein as being used in conjunction with the gastrointestinal tract, it will be recognized by one of skill in the art that the application of the endoscopic device 100 may be expanded to any organs and/or tissues within the body.

FIG. 6 shows a flow chart of one embodiment of a method 300 for performing a surgical operation on the internal body tissue of a patient. For ease of understanding, the steps of the related methods described herein will be discussed relative to the components of the endoscopic device 100 and system 250, but it will be appreciated that any such device and system can be used to perform these methods so long as it has an endoscope, a vacuum port, a vacuum source, and a means for penetrating tissue.

Generally, a physician can utilize the endoscopic device 100 and system 250 as shown in FIGS. 2A-5B to perform an anastomosis procedure completely endoscopically. Specifically, the endoscopic device 100 and system 250 may be used to bypass a portion of the proximal small intestine without making any incisions in the abdominal wall. It will be understood that while the method 300 is described herein as using the device 100 and system 250 and several examples are disclosed where the method 300 is used to perform a surgical bypass of the proximal small intestine (e.g., RYGBP), such examples are not intended to limit the application of the same.

In preparation for the procedure, the outer tubular member 112 and the inner tubular member 162 are positioned in a contracted configuration, such that the inner tubular member 162 does not extend beyond the second end 120 of the outer tubular member 112. In addition, any instruments needed to perform the procedure may be optionally mounted within the endoscopic device 100, such as, for example, the optic system instrument 200 and/or the catheter 190. In preparing the patient for the procedure, suction is applied to the patient's stomach to remove any undigested matter therein and the patient's gastrointestinal tract may be flushed with antibiotics. Thereafter, the patient is placed under general anesthesia.

As shown in FIG. 6, the endoscopic device 100 is inserted through an orifice of the patient at step 302. The endoscopic device 100 is inserted in such a manner that the second end 120 of the outer tubular member 112 is positioned within the body in a location distal of the first end 118 of the outer tubular member 112. Once inserted, the endoscopic device 100 is advanced through the patient's lumen and/or cavities and the second end 120 of the outer tubular member 112 is positioned proximal to the first targeted tissue 40. The precise placement of the second end 120 of the endoscopic device 100 may be facilitated through the use of the optic system instrument 200 (e.g., a fibroscopic instrument or otherwise). In the embodiment where the procedure is used to bypass the proximate small intestine, the orifice comprises the patient's mouth and the first targeted tissue 40 comprises a portion of the interior stomach near or at the greater curvature of the stomach.

At step 304, the vacuum source is operatively connected with the first vacuum port 130 of the endoscopic device 100 and suction is initiated through the first suction port 132. As the second end 120 of the endoscopic device 100 is positioned in proximally to the first targeted tissue 40, the first targeted tissue 40 is sucked into contact with the first suction port 132 of the second end 120 of the outer tubular member 112. Accordingly, a reversible seal is formed between the second end 120 of the outer tubular member 112 and the first targeted tissue 40. Once the reversible seal is formed, if so desired, the first targeted tissue 40 encompassed within the circumference of the outer tubular member 112 may be cleaned and sterilized. This can be achieved by injecting cleaning and sterilization agents into the interior of the first compartment 116 of the outer tubular member 112, either through the first end 118 of the outer tubular member 112 or through some other means. Due to the seal formed between the first suction port 132 and the first targeted tissue 40, containment is achieved and there is little to no risk of stomach acids leaking into the interior of the endoscopic device 100 and onto the first targeted area 40. Accordingly, the method 300 provides for a sterile environment in which the procedure may be performed. The suction delivered to the first targeted tissue 40 through the first suction port 132 is maintained throughout the procedure to ensure that the seal is maintained and the operative area is contained.

Figure 7A:
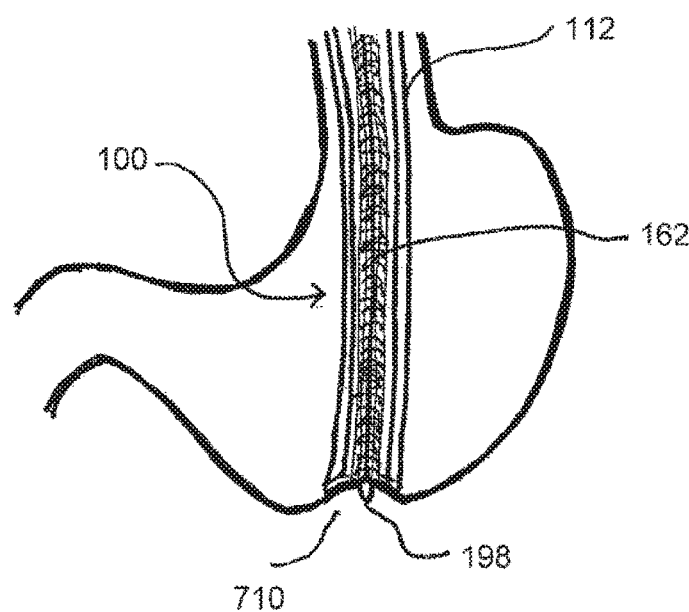
FIG. 7A shows the localization of a tissue using the endoscopic device of FIGS. 2A-5A.
Figure 8A:
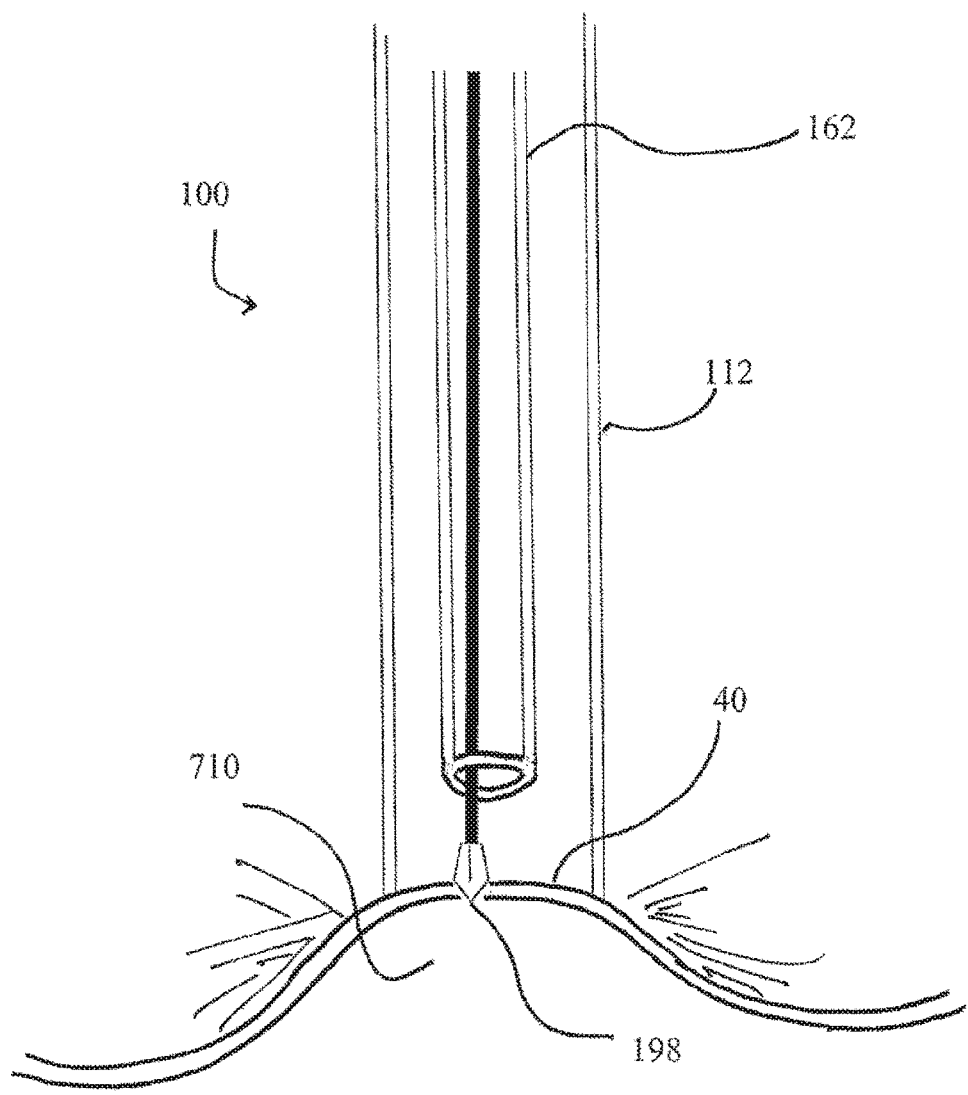

Once the first targeted area 40 is sufficiently cleaned and/or sterilized, the cleaning and sterilization agents may be removed from the interior of the endoscopic device 100 by aspiration or any other means known in the art. For example, aspiration may be supplied through the interior of the first compartment 116, the interior of the second compartment 166 of the inner tubular member 162, or the second suction port 182. At this point, the suction through the first suction port 132 may be increased, such that the first targeted tissue 40 is pulled back by the suctional force and stretched from its typical anatomical position. As shown in FIGS. 7A and 8A, this stretching forms a pocket 710 on the exterior of the first targeted tissue 40, thus pulling the first targeted tissue 40 away from any other organs or tissues disposed in close proximity to the exterior of the first targeted tissue 40 (e.g., colon, liver, intestine, etc.). At step 306, the catheter 190 is advanced through the interior of the second compartment 166 of the inner tubular member 162, thereby advancing the needle 198 disposed thereon and penetrating the first targeted tissue 40 to form a first opening in the first targeted tissue 40.

Figure 7B:
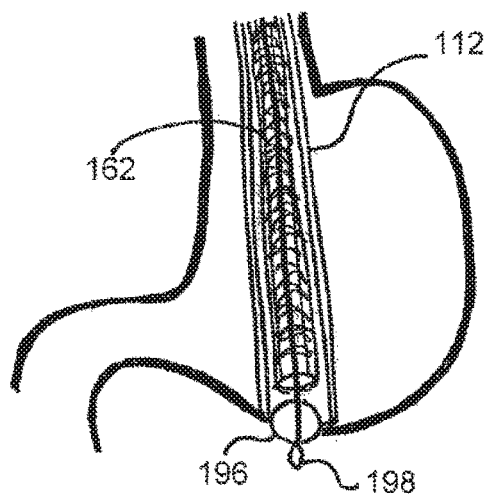
FIG. 7B shows the endoscopic device of FIGS. 2A-5A forming an opening in a targeted tissue.
Figure 8B:
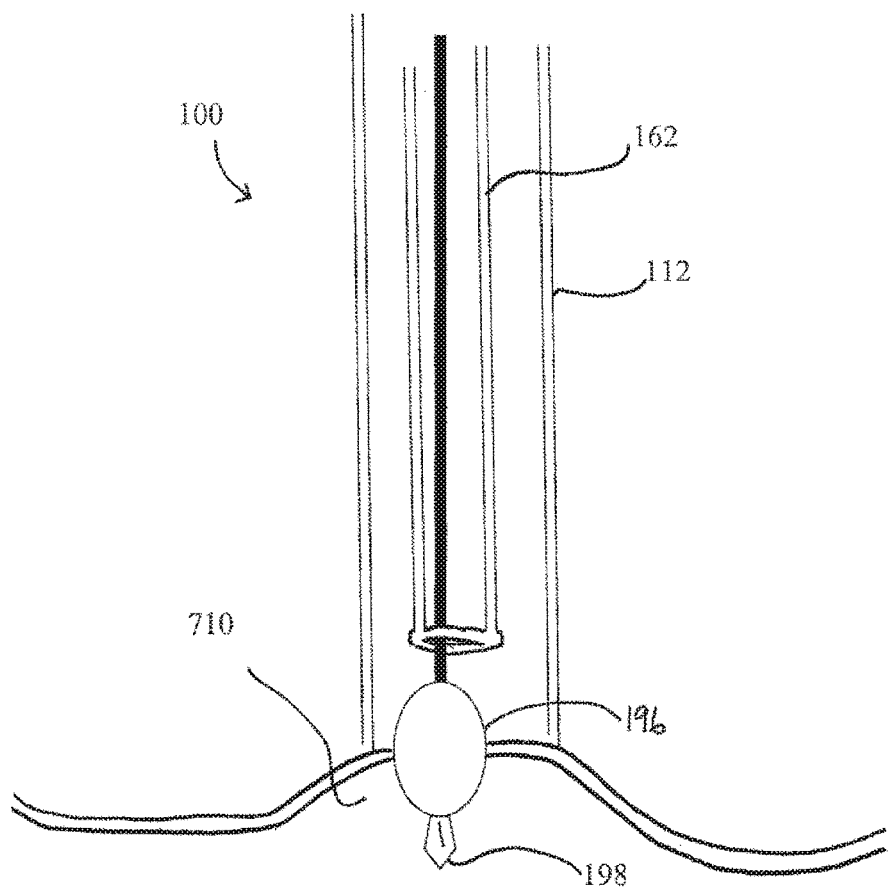
Figure 9A:
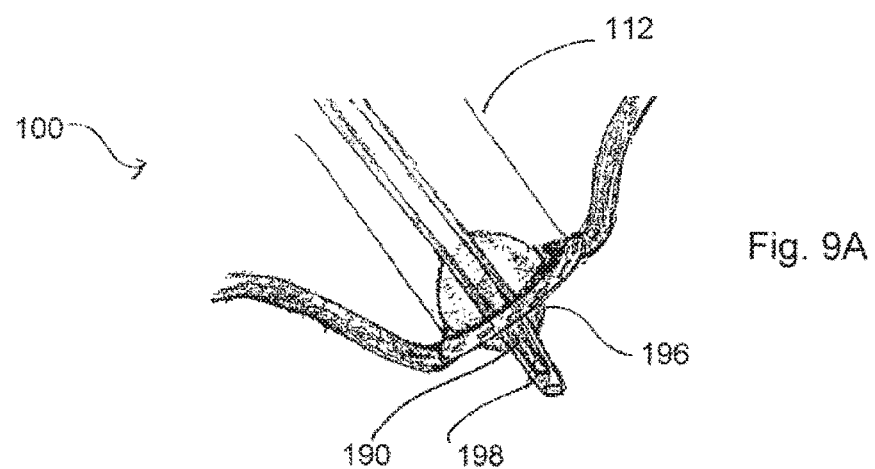
FIGS. 9A to 9B show a cross-sectional view of one embodiment of a balloon catheter disclosed herein in a partially inflated position.
Figure 9B:
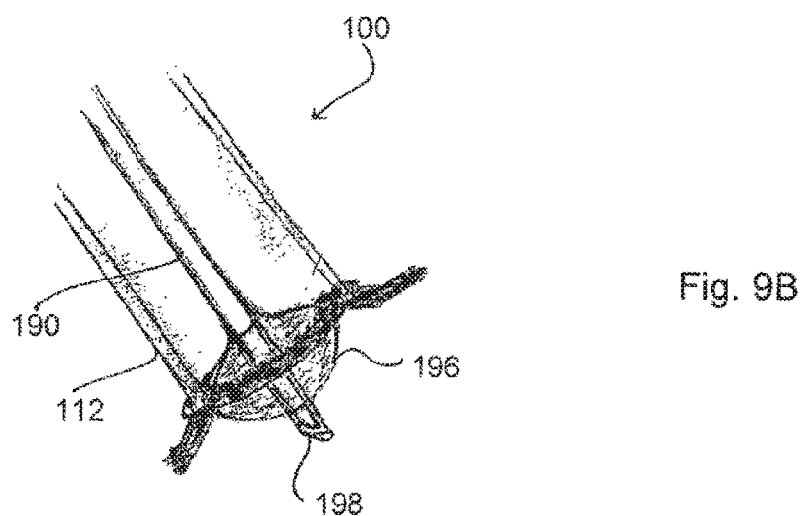

Because the needle 198 has a slender configuration, only a small puncture is made in the first targeted tissue 40, thereby minimizing trauma to the area. The balloon 196, positioned in the first position, is then advanced partially through the first opening in the first targeted tissue 40 as shown in FIGS. 7B and 8B. Once located within the first opening, the balloon 196 is expanded to the second position, thereby dilating the area of the first opening without cutting the tissue and thus reducing the risks of trauma and/or bleeding. The requisite size of the balloon 196 and the first opening may be predetermined by the user and are likely dependent on the characteristics of the individual patient who is undergoing the procedure. It should be noted that the balloon 196 need not be entirely deflated to be advanced through the first opening. For example, as shown in FIGS. 9A and 9B, the balloon 196 is at least partially inflated as it is advanced through the first opening.

At step 308 and as shown in FIGS. 8C-9B, the inner tubular member 162 is telescopically advanced through the second end 120 of the outer tubular member 112 and through the dilated first opening. In the embodiment where the procedure is used to bypass the proximate small intestine, the dilated opening extends through the wall of the greater curvature of the stomach and, when the inner tubular member 162 is advanced through the dilated first opening at step 308, the second end 150 of the inner tubular member 162 is positioned within the peritoneal cavity, outside of the stomach.

At step 310, a second targeted tissue 55 is identified and the vacuum, source is operatively connected with the second vacuum port 180 of the endoscopic device 100 such that suction is initiated through the second suction port 182. The localization of the second targeted tissue 55 may be achieved through the use of the optic system instrument 200. In addition, carbon dioxide may be injected through the second compartment 166 of the inner tubular member 162 to expand the lumen or cavity and thereby increase visceral visualization.

After the second targeted tissue 55 is localized, the second targeted tissue 55 is sucked into contact with the second suction port 182 and a reversible seal is formed therebetween. The suction delivered to the second targeted tissue 55 through the second suction port 182 is maintained throughout the remainder of the procedure to ensure that the reversible seal is maintained and the operative area is contained.

If desired, the second targeted tissue 55 encompassed within the circumference of the inner tubular member 162 can be cleaned and sterilized by injecting cleaning and sterilization agents into the interior of the second compartment 166 of the inner tubular member 162. As described with respect to the seal formed between the outer tubular member 112 and the first targeted tissue 40, the reversible seal formed between the second suction port 182 and the second targeted tissue 55 causes the targeted area on the second targeted tissue 55 to be contained such that there is little to no risk of leakage. For example, when the method 300 is used to bypass the proximate small intestine, the second targeted tissue 55 comprises the exterior of the proximal jejunum.

Figure 10:
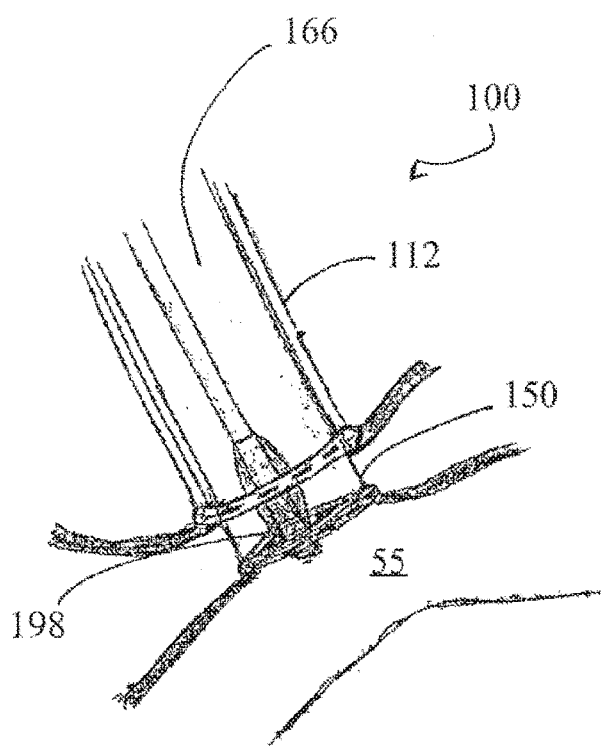
FIG. 10 shows a cross-sectional view of one embodiment of the endoscopic device of FIGS. 2A-5A forming an anastomosis.
Figure 11:
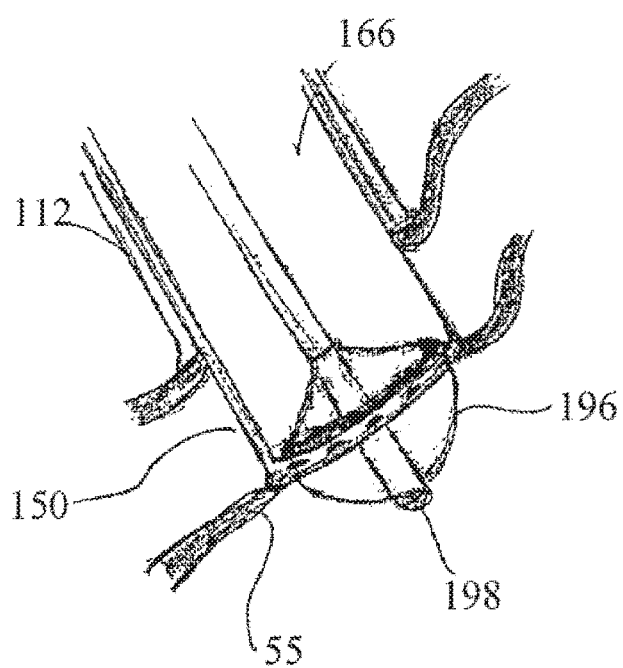
FIG. 11 shows a cross-sectional view of one embodiment of a balloon catheter disclosed herein dilating a second opening in a second targeted tissue.

Once the second targeted area 55 is sufficiently cleaned and sterilized, if so desired, the agents are removed from the interior of the endoscopic device 100 by aspiration or any other means known in the art. As shown in FIG. 10, at step 312, the catheter 190 is again advanced through interior of the second compartment 166, thereby advancing the needle 198 disposed thereon and causing the needle 198 to penetrate the second targeted tissue 55. In this manner, a second opening is formed in the second targeted tissue 55, which is thereafter dilated by the balloon 196 in the same manner as previously described with respect to the first opening of the first targeted tissue 40 (see FIG. 11). Accordingly, through use of the method 300, the telescoping functionality of the endoscopic device 100, among other things, enables a user to access two different body structures completely endoscopically and without forming multiple incisions in the abdominal wall.

After the first and second openings are formed in the first and second targeted tissues 40, 55, respectively, the endoscopic device 100 can be maneuvered so as to concentrically align the first dilated opening and the second dilated opening and bring the two openings within close proximity to one another. For example, this may be accomplished by retracting the second end 150 of the inner tubular member 162 back into the interior 116 of the outer tubular member 112. In the example where the method 300 is used to bypass the proximate small intestine from the digestive process, the second end 150 of the inner tubular member 162 can be manipulated to move the jejunal portion of the small intestine into close proximity or even contact with the exterior stomach wall.

Figure 12A:
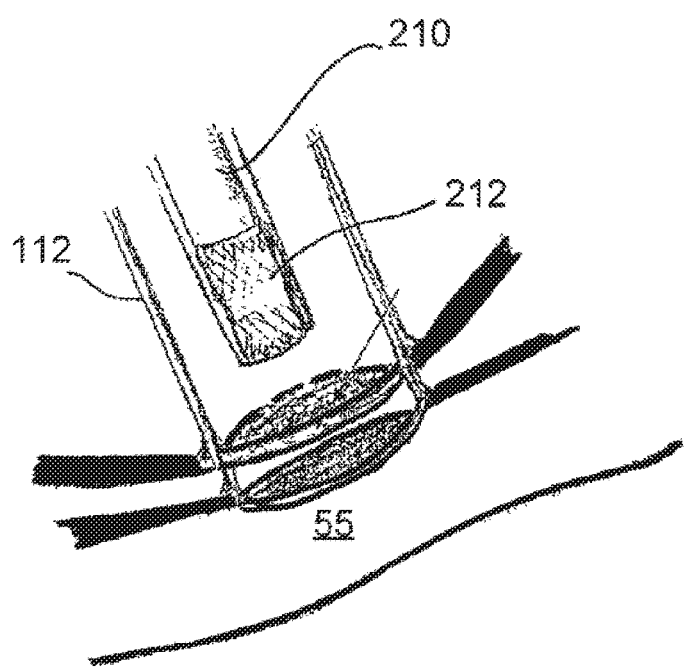
FIGS. 12A, 12B, and 13 show cross-sectional views of one embodiment of a stent delivery device, disclosed herein delivering a stem to form an anastomosis.

At step 314, and as shown in FIG. 12A, the stent delivery device 210 with a stern 212 coupled thereto may be used to deploy the stent 212 within the two openings in the first and second tissues 40, 55, thereby forming an anastomosis therebetween. It will be understood that any type of stent is sufficient to use in conjunction with the method 300 so long as the stent 212 is capable of securing to both the first and second targeted tissues 40, 55 and forming abridge therebetween. Accordingly, at step 314, the stern delivery device 210 containing the stent 212 positioned in the first, compressed position is advanced through the interior of the second compartment 166 of the inner tubular member 210 and into the dilated first and second openings in the first and second targeted tissues 40, 55, respectively. Optionally, the stein delivery device. 210 may be used in conjunction with the optic system instrument 200 to ensure the accurate placement of the stent 212 within the two dilated openings at step 316.

Figure 12B:
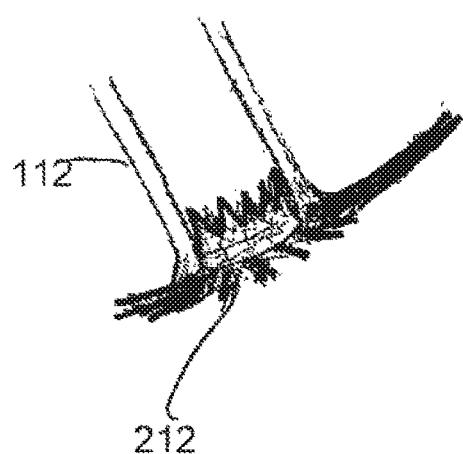

At step 318, and as shown in FIG. 12B, the stent 212 is deployed within the two openings. For example, the stent delivery device 212 may first deploy the stent 212 within the second opening in the second targeted tissue 55 such that the stent 212 engages with the second targeted tissue 55. When the stein 212 has been securely coupled with the second targeted tissue 55, the stent 212 supplies support to the second opening and, thus, the suction through the second suction ports 182 may be ceased and the second end 150 of the inner tubular member 162 can be retracted into the outer tubular member 112.

Figure 13:
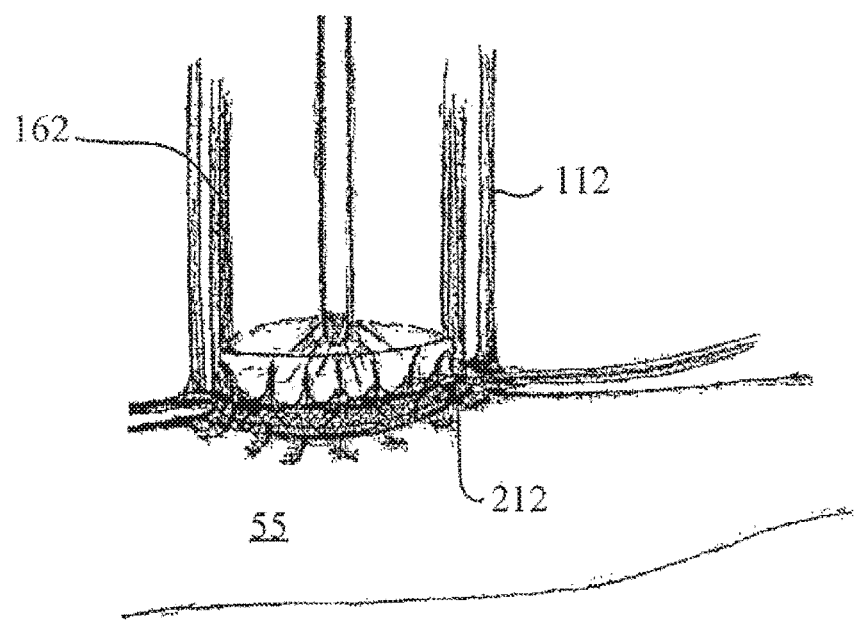
Figure 14:
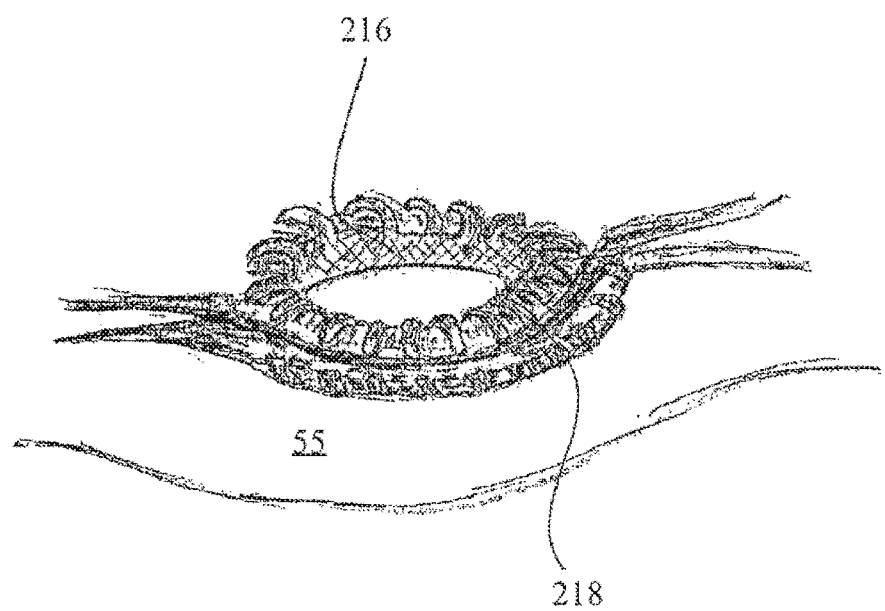
FIG. 14 shows an anastomosis formed using an embodiment of the stent disclosed herein.
Figure 15:
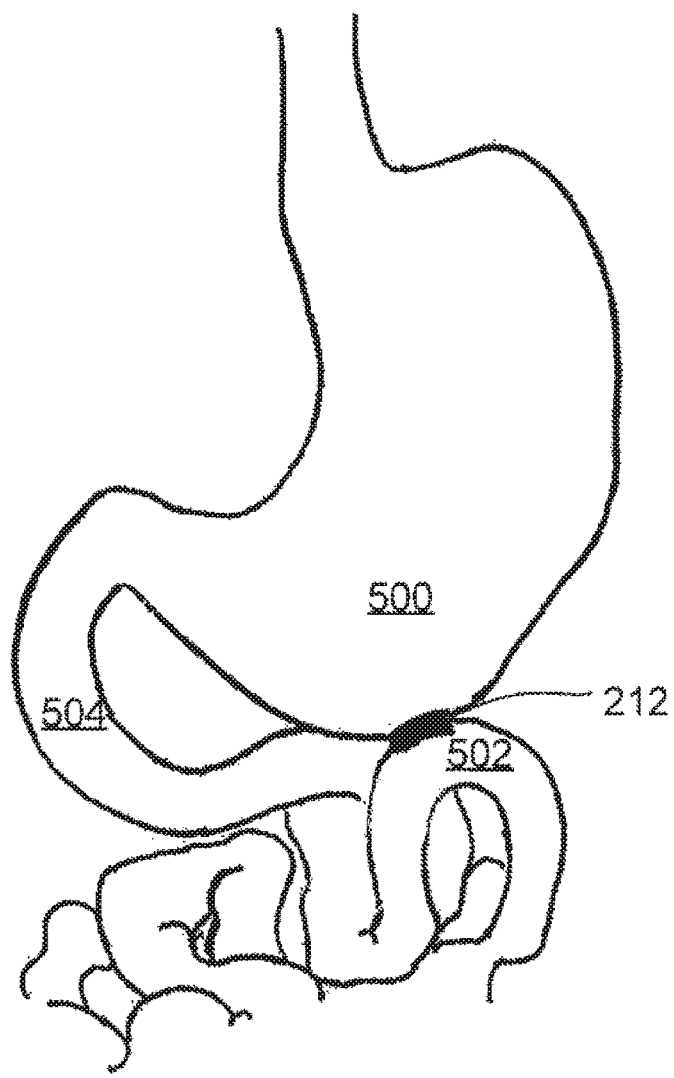
FIG. 15 shows a front view of a duodenal bypass using one embodiment of a method and endoscopic device disclosed herein.

Thereafter, the stent delivery device 210, optionally under the control of an optic system instrument 200, is slightly withdrawn through the interior of the second compartment 166 of the inner tubular member 210 such that the stein delivery device 210 approaches the first opening in the first targeted tissue 40. After being properly positioned, the second part of the stent 212 is deployed therein, thereby releasing the stent 212 from the stein delivery device 210, engaging the stent 212 with the first targeted tissue 40, and sealing the anastomosis. As seen in FIGS. 13 and 14, the deployed stent 212 forms a bridge or anastomosis between the two tissue openings such that a secure connection is formed therebetween. In the embodiment where the method 300 is used to bypass the proximate small intestine, by deploying the stent 212 within the two openings, an anastomosis is formed that connects the interior of a stomach 500 directly with the interior of a jejunum 502 of the small intestine. In this manner, a duodenum 504 of the small intestine may be bypassed from digestion see FIG. 15).

Figure 16:
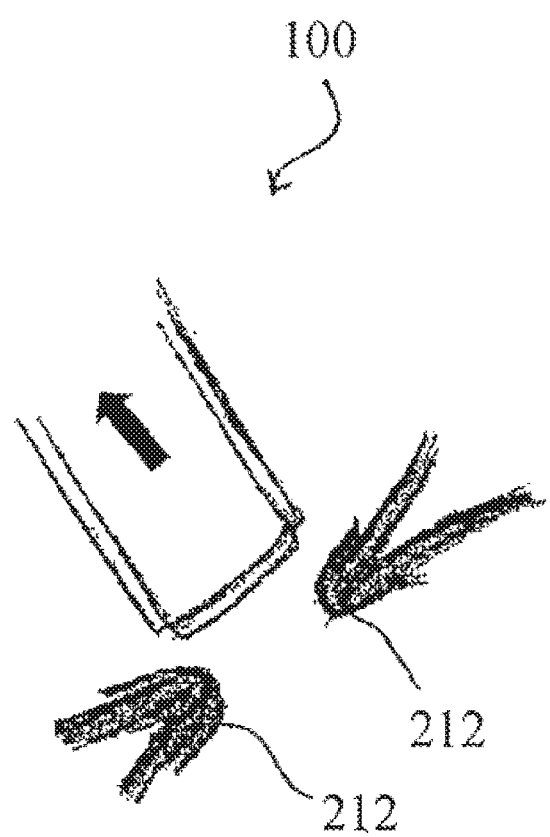
FIG. 16 shows the endoscopic device being withdrawn from a completed anastomosis.

After the anastomosis is sealed, the stem 212 is released from the stent delivery device 210. Under the surveillance of the optic system instrument 200, the remaining suction through the first suction port 132 is ceased and the outer tubular member 112 is removed from the body as shown in FIG. 16.

Figure 17:
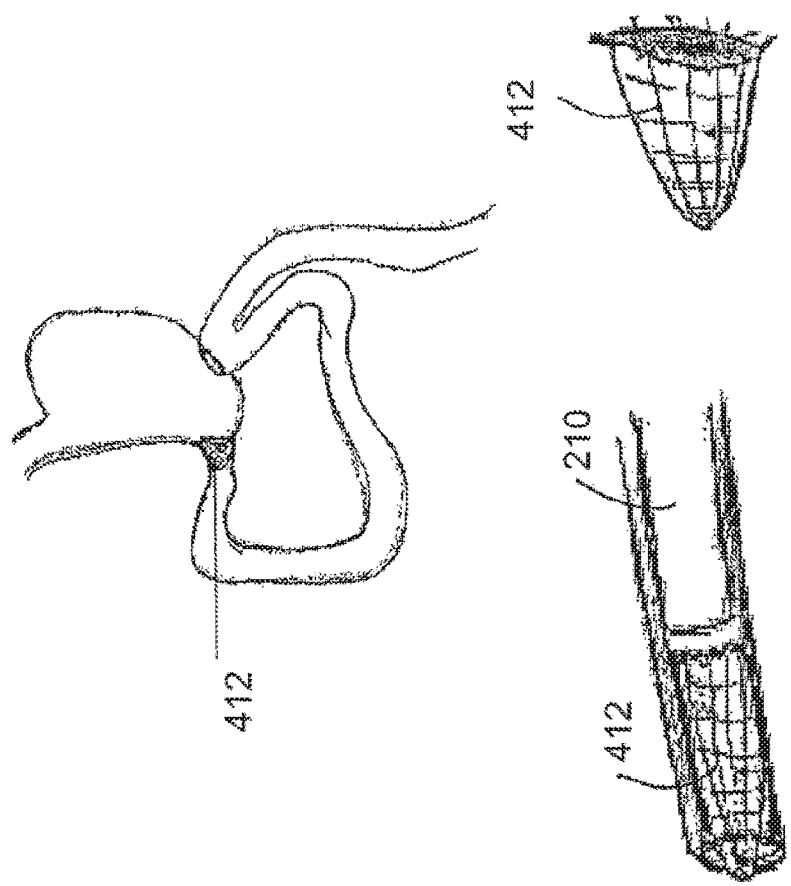
FIG. 17 shows one embodiment of an occlusion stent as disclosed herein.

In the embodiment where the method 300 is used to bypass the proximate small intestine, it is further necessary to occlude the natural passage of digested matter through the pylorus. Accordingly, a compressed stent occluder 412 may be coupled with the distal end of the stent delivery device 210 and endoscopically positioned within the prepyloric area of the stomach as shown in FIGS. 17A and 17B. It will be understood that while a conical stent occluder is illustrated in FIGS. 17A and 17B, any type and/or configuration of a stein occluder may be used to occlude the natural passage of digested matter through the pylorus. By occluding the gastric outflow through the pylorus through the use of the stent occluder 412, total isolation of the duodenum is achieved and any digested matter contained within the stomach is forced to leave the stomach cavity through the anastomosis.

While various embodiments of devices, systems, and methods for accessing various tissues endoscopically have been described in considerable detail herein, the embodiments are merely offered by way of non-limiting examples. Many variations and modifications of the embodiments described herein will be apparent to those of ordinary skill in the art in light of this disclosure. It will therefore be understood by those of ordinary skill in the art that various changes and modifications may be made, and equivalents may be substituted for elements thereof, without departing from the scope hereof. Indeed, this disclosure is not intended to be exhaustive or limiting. The scope of this disclosure is to be defined by the appended claims, and by their equivalents.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps disclosed herein should not be construed as limitations on the claims. In addition, the claims directed to a method and/or process should not be limited to the performance of their steps in the order written, and one skilled in the art can readily appreciate that the sequences may be varied and still remain within the spirit and scope of the present disclosure.

The invention claimed is:

1. A method for performing an endoscopic procedure, comprising:
    inserting an endoscopic device into a patient, the endoscopic device comprising:
        an outer tubular member and an inner tubular member, the outer tubular member and the inner tubular member each comprising a proximal end, a distal open end, a vacuum channel in communication with a suction port at the distal open end, and a compartment;
        the inner tubular member is slidably disposed within the compartment of the outer tubular member such that the distal open end of the inner tubular member can advance through the distal open end of the outer tubular member;
    engaging the distal open end of the outer tubular member with a first targeted tissue;
    supplying suction through the vacuum channel of the outer tubular member to form a reversible seal under vacuum between the suction port of the outer tubular member and the first targeted tissue;
    penetrating the first targeted tissue with a catheter slidably disposed within the compartment of the inner tubular member such that a first opening is formed in the first targeted tissue;
    advancing the inner tubular member through the first opening in the first targeted tissue;
    supplying suction through the vacuum channel of the inner tubular member to form a reversible seal under vacuum between the suction port of the inner tubular member and a second targeted tissue;
    penetrating the second targeted tissue with the catheter such that a second opening is formed in the second targeted tissue;
    retracting the inner tubular member through the distal open end of the outer tubular member to pull the second opening in the second targeted tissue into close proximity and substantially concentric alignment with the first opening in the first targeted tissue using suction through the vacuum channel of the inner tubular member to maintain engagement with the second targeted tissue;
    positioning a first stent at least partially within the first and second openings of the targeted tissues through operation of a stent delivery device slidably disposed within the compartment of the inner tubular member; and
    forming a sealed anastomosis between the first and second openings by deploying the first stent.

2. The method of claim 1, wherein the outer tubular member further comprises a first vacuum port in communication with at least one of the vacuum channel and compartment of the outer tubular member and the inner tubular member further comprises a second vacuum port in communication with at least one of the vacuum channel and compartment of the inner tubular member and supplying suction through the vacuum channel of the outer tubular member and supplying suction through the vacuum channel of the inner tubular member further comprises operatively connecting at least one vacuum source to the first and second vacuum ports.

3. The method of claim 1, further comprising:
    wherein the vacuum channel of the outer tubular member is disposed around the circumference of the outer tubular member such that the compartment is wholly surrounded by the vacuum channel of the outer tubular member and the vacuum channels extend to the distal open end.

4. The method of claim 1, further comprising:
    cleaning and sterilizing the first targeted tissue prior to penetrating the first targeted tissue with the catheter, and
    cleaning and sterilizing the second targeted tissue prior to penetrating the second targeted tissue with the catheter.

5. The method of claim 1, wherein the first targeted tissue comprises an interior wall of a stomach in a location proximal to a greater curvature of the stomach, and the second targeted tissue comprises an exterior wall of a small intestine in a location proximal to a proximal jejunum.

6. The method of claim 5, further comprising:
    endoscopically inserting a second stent into the pylorus of the stomach such that the pylorus is occluded and digested matter is prevented from flowing therethrough.

7. The method of claim 1, further comprising:
    an optic system instrument slidably disposed directly within the compartment of the inner tubular member and further comprising using the optic system instrument to visually locate the first targeted tissue and the second targeted tissue.

8. The method of claim 1, wherein the catheter further comprises a dilation implement.

9. The method of claim 8, wherein the dilation implement of the catheter comprises a balloon adapted to move between a first deflated position and a second inflated position and further comprising the steps of:
    advancing the balloon in the first deflated position into the first opening of the first targeted tissue;
    dilating the balloon into the second inflated position such that the first opening increases in diameter;
    deflating and advancing the balloon into the second opening of the second targeted tissue; and
    dilating the balloon into the second inflated position such that the second opening increases in diameter.

10. The method of claim 8, wherein the catheter further comprises a needle extending distally from the catheter.

11. The method of claim 9, wherein the first deflated position comprises a first diameter and the second inflated position comprises a second diameter, wherein the first diameter is less than the second diameter.

12. The method of claim 1, further comprising:
    increasing the suction through the vacuum channel of the outer tubular member such that the first targeted tissue is temporarily displaced from its normal anatomical position in the body.

13. A method for performing a surgical operation on internal body tissues of a patient comprising:

inserting at least part of an endoscopic device of a system into the patient, the system comprising:
the endoscopic device comprising:
an outer tubular member comprising:
a first vacuum channel comprising a first vacuum port, a first suction port, and an interior, and the first suction port configured to removably attach to a first targeted tissue,
a first compartment comprising an interior,
a first proximal end, and
a second distal end in operative communication with the first suction port,
an inner tubular member slidably disposed within the interior of the first compartment of the outer tubular member, the inner tubular member comprising:
a second vacuum channel comprising a second vacuum port, a second suction port, and an interior, and the second suction port configured to removably attach to a second targeted tissue,
a second compartment,
a first proximal end, and
a second distal end in operative communication with the second suction port,
wherein the second distal end of the inner tubular member is capable of extending through the second distal end of the outer tubular member;
a catheter slidably disposed within an interior of the second compartment, the catheter comprising a first end and a second end and wherein the second end of the catheter comprises a means for penetrating the first and second targeted tissues and a means for dilation;
a stent delivery device slidably disposed directly within the interior of the second compartment such that the stent delivery device can be inserted and withdrawn from the interior of the second compartment independent of the catheter, the stent delivery device comprising a first end and a second end, wherein the second end is capable of removably coupling with a stent; and
a first stent removably coupled with the second end of the stent delivery device, wherein the first stent is capable of forming an anastomosis between the first and second tissues and;
supplying suction through the first vacuum port such that the first suction port of the outer tubular member forms a reversible seal with the first targeted tissue;
penetrating the first targeted tissue with the means for penetrating the first and second targeted tissues such that a first opening is formed in the first targeted tissue;

advancing the inner tubular member through the second distal end of the outer tubular member and through the first opening in the first targeted tissue;
supplying suction through the second vacuum port such that the second suction port of the inner tubular member forms a reversible seal with the second targeted tissue;
penetrating the second targeted tissue with the means for penetrating the first and second targeted tissues such that a second opening is formed in the second targeted tissue;
retracting the inner tubular member through the second distal end of the outer tubular member to pull the second opening into close proximity and substantially concentric alignment with the first opening in the first targeted tissue using suction through the second suction port to maintain engagement with the second targeted tissue;
slidably inserting the stent delivery device and the first stent into the interior of the inner tubular member;
positioning the first stent partially within the first and second openings; and
deploying the first stent to form a sealed anastomosis between the first and second openings.

14. The method of claim 13, further comprising:
wherein the second vacuum channel is disposed around the circumference of the inner tubular member such that the second compartment is wholly surrounded by the second vacuum channel and the second vacuum channel extends to the second distal end of the inner tubular member.

15. The method of claim 13, wherein the first targeted tissue comprises an interior wall of a stomach in a location proximal to the greater curvature of the stomach, and the second targeted tissue comprises an exterior wall of a small intestine in a location proximal to the proximal jejunum.

16. The method of claim 15, further comprising endoscopically inserting a second stent into a pylorus of the stomach such that a portion of the pylorus is occluded and digested matter is prevented from flowing therethrough.

17. The method of claim 13, wherein the system further comprises an optic system instrument slidably disposed directly within the second compartment of the inner tubular member and further comprising using the optic system instrument to visually locate the first targeted tissue and the second targeted tissue.

* * * * *